(12) United States Patent
Lieberman et al.

(10) Patent No.: US 8,481,698 B2
(45) Date of Patent: Jul. 9, 2013

(54) PARALLEL PROXIMITY LIGATION EVENT ANALYSIS

(75) Inventors: Erez Lieberman, Cambridge, MA (US); Andreas Gnirke, Wellesley, MA (US); Daniel Aird, Medford, MA (US)

(73) Assignees: The President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 387 days.

(21) Appl. No.: 12/407,547

(22) Filed: Mar. 19, 2009

(65) Prior Publication Data
US 2010/0240101 A1   Sep. 23, 2010

(51) Int. Cl.
*C12N 15/11*  (2006.01)
*C07H 21/04*  (2006.01)

(52) U.S. Cl.
USPC .................................................... 536/23.1

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 4,981,785 A | 1/1991 | Nayak | 435/7.94 |
| 5,358,691 A | 10/1994 | Clark et al. | 422/64 |
| 5,538,848 A | 7/1996 | Livak et al. | 435/6.16 |
| 5,599,677 A | 2/1997 | Dowell et al. | 435/7.4 |
| 5,639,606 A | 6/1997 | Willey | 435/6.12 |
| 5,643,765 A | 7/1997 | Willey | 435/91.2 |
| 5,672,480 A | 9/1997 | Dowell et al. | 435/7.4 |
| 5,846,717 A | 12/1998 | Brow et al. | 435/6.18 |
| 5,876,978 A | 3/1999 | Willey et al. | 435/91.2 |
| 5,885,530 A | 3/1999 | Babson et al. | 422/65 |
| 5,985,557 A | 11/1999 | Purdent et al. | 435/6.1 |
| 5,994,069 A | 11/1999 | Hall et al. | 435/6.18 |
| 6,001,567 A | 12/1999 | Brow et al. | 435/5 |
| 6,090,543 A | 7/2000 | Prudent et al. | 435/6.18 |
| 6,159,750 A | 12/2000 | Edmonds | 436/537 |
| 6,268,490 B1 | 7/2001 | Imaniski et al. | 536/23.1 |
| 7,427,479 B2 | 9/2008 | Karger et al. | 435/6.1 |
| 2008/0044834 A1* | 2/2008 | Heyduk | 435/6 |

OTHER PUBLICATIONS

Ahern, The Scientist 9 (15), 20 (1995).*
Anderson, M.L.M. and B.D. Young. 1985, Quantitative filter hybridization, p. 73-111. In. Hames B.D. and S.J. Higgins (Eds), Nucleic Acid Hybridisation: A Practical Approach.
Aronoff et al., "Eicosanoids in non-febrile thermoregulation," *Prog Brain Res* 162:15-25 (2007).
Baner et al., "Signal amplification of padlock probes by rolling circle replication," *Nucleic Acids Res.* 26:5073-5078 (1998).
Bolhuis et al., "Engineering T lymphocyte antigen specificity," *J. Cell. Biochem.* 47:306-310 (1991).
Braunewell et al., "Visinin-like proteins (VSNLs): interaction partners and emerging functions in signal transduction of a subfamily of neuronal Ca2+-sensor proteins," *Cell Tissue Res.* 335(2):301-316 (2009).
Breuner, C. W. and Orchinik, M., "Pharmacological characterization of intracellular, membrane, and plasma binding sites for corticosterone in house sparrows," *Gen. Comp. Endocrinol.* 163(1-2), 214-224 (2009).
Bustin M.., "Chromatin unfolding and activation by HMGN chromosomal protein,s" *Trends Biochem Sci.* 26:431-437 (2001).
Clarke et al., "Spatial and temporal coordination of mitosis by Ran GTPase," *Nat Rev Mol Cell Biol.* 9:464-477 (2008).
Déjardin, J. and Kingston, R. E., "Purification of Proteins Associated with Specific Genomic Loci," *Cell* 136(1), 175-186 (2009).
Erlich et al., "Recent advances in the polymerase chain reaction," *Science* 252:1643-1651 (1991).
Fredriksson et al., "Multiplexed protein detection by proximity ligation for cancer biomarker validation," *Nature Methods* 4:327-329 (2007).
Fredriksson et al., "Protein detection DNA using proximity-dependent ligation assays," *Nature Biotechnology* 20:473-477 (2002).
Geisow, M. J., "Improved selection systems for man-made antibodies," *Trends Biotechnol.* 10:75-76 (1992).
Green et al., "Inhibitory DNA ligands to platelet-derived growth factor B-chain," *Biochemistry* 45:14413-14424 (1996).
Gustafsson JA., "Receptor-mediated toxicity," *Toxicol Lett.* 82-83:465-470 (1995).
Hardenbol et al., "Multiplexed genotyping with sequence-tagged molecular inversion probed," *Nat. Biotechnol.* 21:673-678 (2003).
Jensen et al., "Proteins on the move: dynamic protein localization in prokaryotes," *Trends Cell Biol.* 10:483-488 (2000).
Kaur et al., "Thermodynamic, counterion and hydration effects for the incorporation of locked nucleic acid (LNA) nucleotides in duplex," *Nucleic Acids Symp Ser (Oxf).* 52:425-426 (2008).
Kibbey et al., "Molecular property explorer: a novel approach to visualizing SAR using tree-maps and heatmap,s" *J Chem InfModel.* 45:523-32 (2005).

(Continued)

*Primary Examiner* — James Martinell
(74) *Attorney, Agent, or Firm* — Medlen & Carroll, LLP

(57) ABSTRACT

The present invention describes compositions and methods showing that the spatial proximity of intracellular components may be related to their ability to cooperate in intracellular biochemical reactions. In some embodiments, the present invention contemplates a variety of nucleic acid barcoded binding partners capable of determining the spatial proximity of intracellular components as determined by ligation of their respective nucleotide barcodes. As such, an intracellular component contact map may be constructed to fingerprint specific physiological and/or pharmacological intracellular conditions.

24 Claims, 23 Drawing Sheets
(1 of 23 Drawing Sheet(s) Filed in Color)

OTHER PUBLICATIONS

Koehler and Milstein, "Continuous cultures of fused cells secreting antibody of predefined specificity," *Nature* 256:495-7 (1975).

Kozlov, I.A., "Efficient strategies for the conjugation of oligonucleotides to antibodies enabling highly sensitive protein detection," *Biopolymers* 73:621-30 (2004).

Lee HC., "Specific binding of cyclic ADP-ribose to calcium-storing microsomes from sea urchin eggs," *J Biol Chem.* 266:2276-2281 (1991).

Lerner et al., "At the crossroads of chemistry and immunology: catalytic antibodies," *Science* 252:659-67 (1991).

Maelfait et al., "Stimulation of Toll-like receptor 3 and 4 induces interleukin-1β maturation by caspase-8," *J Exp Med.* 205:1967-1973 (2008).

Maniatis, T. et al., "Regulation of inducible and tissue-specific gene expression," *Science* 236:1237-1245 (1987).

Mazars et al., "Organization of cytoskeleton controls the changes in cytosolic calcium of cold-shocked *Nicotiana plumbaginifolia* protoplasts," *Cell Calcium* 22:413-20 (1997).

McDonnell et al., "Nuclear hormone receptors as targets for new drug discovery," *Biotechnology* (NY) 11:1256-1261 (1993).

Mestries et al., "Interactions between 25 biospecific polymers and MCF7 cells: modulation of cellular proliferation and expression of estrogen receptors," *Bull Cancer.* 84:1017-1023 (1997).

Oberleithner et al., "Aldosterone and nuclear volume cycling," *Cell Physiol Biochem* 10:429-434 (2000).

Pitcher et al., "Role of βγ subunits of G proteins in targeting the β-adrenergic receptor kinase to membrane-bound receptors," *Science* 257:1264-1267 (1992).

Rawe et al., "WAVE1 intranuclear trafficking is essential for genomic and cytoskeletal dynamics during fertilization: cell-cycle-dependent shuttling between M-phase and interphase nuclei," *Dev Biol.* 276:253-267 (2004).

Ron et al., "Cloning of an intracellular receptor for protein kinase C: a homolog of the beta subunit of G proteins," *Proc Natl Acad Sci U S A.* 91:839-843 (1994).

Ryan et al., "Temporal and spatial regulation in prokaryotic cell cycle progression and development," *Annu Rev Biochem.* 72:367-394 (2003).

Saiki, R. K. et al., "Enzymatic amplification of β-globin genomic sequences and restriction site analysis for diagnosis of sickle cell anemia." *Science* 230:1350-1354 (1985).

Sano et al., "Immuno-PCR: very sensitive antigen detection by means of specific antibody-DNA conjugates," *Science* 258:120-122 (1992).

Satoh et al., "The inositol 1,4,5,-trisphosphate receptor in cerebellar Purkinje cells: quantitative immunogold labeling reveals concentration in an ER subcompartment" *J Cell Biol.* 111:615-624 (1990).

Singh et al, "LNA 9locked nucleic acids): synthesis and high-affinity nucleic acid recognition." *Chem. Comm.* 455-456 (1998).

Soderberg et al., "Direct observation of individual endogenous protein complexes in situ by proximity ligation," *Nature Methods* 3:995-1000 (2006).

Sugden et al., "Endothelin signalling in the cardiac myocyte and its pathophysiological relevance," *Curr Vasc Pharmacol.* 3:343-351 (2005).

Thijssen JH., "Gene polymorphisms that may influence the biological effects of progestins," *Maturitas* 62:366-370 (2009).

Thyberg et al., "Phenotype modulation in primary cultures of rat aortic smooth muscle cells. Effects of drugs that interfere with the functions of the vacuolar system and the cytoskeleton," *Virchows Arch B Cell Pathol Incl Mol Pathol.* 59:1-10 (1990).

Wegener et al., "Effects of nitric oxide donors on cardiac contractility in wild-type and myoglobin-deficient mice," *Br JPharmacol.* 136:415-420 (2002).

Wengel J., "Synthesis of 3'-c-and $'-c-branched oligodeoxynucleotides and the development of locked nucleic acid (LNA)," *Acc. Chem. Res.,* 32:301-310 (1998).

Yu et al., "Effect of cell type on the subcellular localization of the thyrotropin-releasing hormone receptor," *Mol Pharrnacol.* 51:785-793 (1997).

Zhang et al., "Interactive analysis of systems biology molecular expression data," *BMC Syst Biol.* 2:23 (2008).

\* cited by examiner

A.

B.

C.

A.

B.

C.

D.

PARALLEL PROXIMITY LIGATION EVENT ANALYSIS

STATEMENT OF GOVERNMENT SUPPORT

This invention was made with government support under grant number 5-U54-HG003067-06 awarded by the National Institutes of Health. The government has certain rights in this invention.

FIELD OF INVENTION

The present invention is related to the field of intracellular biochemistry. For example, the spatial proximity of intracellular components may be related to their ability to cooperate in intracellular biochemical reactions. In some embodiments, the present invention contemplates a variety of nucleic acid barcoded binding partners capable of determining the spatial proximity of intracellular components as determined by ligation of their respective nucleotide barcodes. As such, an intracellular component contact map may be constructed to fingerprint specific physiological and/or pharmacological intracellular conditions.

BACKGROUND

It is often of great interest to determine whether two cellular components are in close proximity to one another. For instance, there are several existing methods for determining proteins with the tendency to form complexes, such as Yeast 2-hybrid and mass spectroscopy. These methods require separate experiments for each protein of interest and cannot be used to probe other cellular components such as nucleic acids (DNA and RNA) and small molecules. In addition, they do not take advantage of the plummeting cost of sequencing.

Further, current methods to provide intracellular localization of individual proteins and/or enzymes only provides partial information. These studies have no relevance as to whether these proteins are actively participating in an intracellular biochemical function, or merely being transported from one intracellular region to another. Further, these methods do not provide information regarding hundreds if not thousands of biochemical functions that are occurring simultaneously.

Clearly what is needed are compositions and methods that are amenable to high throughput technology that can accurately provide real time information regarding the interactions between potentially all intracellular components at the same time.

SUMMARY

The present invention is related to the field of intracellular biochemistry. For example, the spatial proximity of intracellular components may be related to their ability to cooperate in intracellular biochemical reactions. In some embodiments, the present invention contemplates a variety of nucleic acid barcoded binding partners capable of determining the spatial proximity of intracellular components as determined by ligation of their respective nucleotide barcodes. As such, an intracellular component contact map may be constructed to fingerprint specific physiological and/or pharmacological intracellular conditions.

In one embodiment, the present invention contemplates a composition comprising a binding partner attached to a unique nucleotide barcode sequence. In one embodiment, the binding partner is selected from the group consisting of an antibody, a locked nucleic acid, a receptor, a derivatized bead, a biological cell, and a small organic molecule. In one embodiment, the unique nucleotide barcode sequence comprises a specific primer pair sequence. In one embodiment, the unique nucleotide barcode sequence comprises a first stand and a second strand. In one embodiment, the first strand comprises a '3 primer sequence and a 5' primer sequence. In one embodiment, the first strand comprises a first nucleic acid sequence and a linker molecule. In one embodiment, the second strand comprises a second nucleic acid sequence, wherein said second nucleic acid sequence is complementary to said first nucleic acid sequence. In one embodiment, the linker molecule attaches said first strand to said binding partner.

In one embodiment, the present invention contemplates a composition comprising a binding partner attached to a forked adapter molecule. In one embodiment, the binding partner is selected from the group consisting of an antibody, a locked nucleic acid, a receptor, a derivatized bead, a biological cell, and a small organic molecule. In one embodiment, the forked adapter molecule comprises a unique nucleotide barcode sequence. In one embodiment, the forked adapter molecule comprises a first stand and a second strand. In one embodiment, the first strand comprises a first nucleic acid sequence and a linker molecule. In one embodiment, the second strand comprises a second nucleic acid sequence, wherein said second nucleic acid sequence is complementary to said first nucleic acid sequence. In one embodiment, the linker molecule attaches said first strand to said binding partner.

In one embodiment, the present invention contemplates a composition comprising a nucleic acid sequence having a 3'-5' first strand and a 5'-3' second strand, wherein said first strand 3' end is attached to a first binding partner and said second strand 3' end is attached to a second binding partner. In one embodiment, the first strand 3' end further comprises a first primer. In one embodiment, the first strand 5' end further comprises a second primer. In one embodiment, the nucleic acid sequence comprises an asymmetric nucleotide barcode sequence. In one embodiment, the first binding partner is selected from the group consisting of an antibody, a locked nucleic acid, a receptor, a derivatized bead, a biological cell, and a small organic molecule. In one embodiment, the second binding partner is selected from the group consisting of an antibody, a locked nucleic acid, a receptor, a derivatized bead, a biological cell, and a small organic molecule.

In one embodiment, the present invention contemplates a method, comprising: a) providing; i) a first binding partner having affinity for a first intracellular component, wherein said first binding partner is attached to a first unique nucleotide barcode sequence; ii) a second binding partner having affinity for a second intracellular component, wherein said second binding partner is attached to a second unique nucleotide barcode sequence; iii) a biological sample comprising said first and second intracellular components; and b) contacting said first and second binding partners with said sample under conditions such that an asymmetric nucleotide barcode sequence is created. In one embodiment, the contacting further comprises binding said first binding partner to said first intracellular component. In one embodiment, the contacting further comprises binding said second binding partner to said second intracellular component. In one embodiment, the first unique nucleotide barcode comprises double stranded deoxyribonucleic acid. In one embodiment, the second unique nucleotide barcode comprises double stranded deoxyribonucleic acid. In one embodiment, the contacting further comprises ligating said first double stranded unique nucleotide barcode and said second double stranded unique nucleotide barcode.

In one embodiment, the first single stranded deoxyribonucleic acid comprises a unique nucleotide barcode and a self-complementary sequence at the 3' end. In one embodiment, the second deoxyribonucleic acid comprises a unique nucleotide barcode and the same self-complementary sequence at the 3' end. In one embodiment, the single-stranded deoxyribonucleotides contain a uracil 5' to the unique nucleotide barcodes. In one embodiment, the contacting further comprises annealing said first single stranded nucleotide and said second single stranded nucleotide via the common self-complementary sequence at the 3'-ends followed by bi-directional primer extension of each 3'-end, thereby creating a double stranded deoxyribonucleic acid sequence that comprises the asymmetric nucleotide barcode sequence. In one embodiment, the primers are extended by a DNA-dependent DNA polymerase. In one embodiment, the primers are extended by a reverse transcriptase. In one embodiment, the method further comprises cleaving said double-stranded asymmetric nucleotide barcode sequence formed by primer extension off the two binding partners, followed by ligation to suitable adapters thereby forming amplicons that can be PCR amplified. In one embodiment, cleavage is carried out by enzymatic excision of the uracil-containing nucleoside in the double-stranded product of the primer extension followed by enzymatic cleavage of the phosphodiester bond on the complementary strand directly opposite to the gap left after excision of the uracil-containing nucleoside. Enzymes that catalyze the uracil excision and phosphodiester cleavage are well know to those skilled in the art.

In one embodiment, the first unique nucleotide barcode comprises single stranded deoxyribonucleic acid. In one embodiment, the second unique nucleotide barcode comprises single stranded deoxyribonucleic acid. In one embodiment, the first single stranded nucleotide comprises a first sequence complementary to a first primer. In one embodiment, the second unique nucleotide barcode comprises a second sequence complementary to a second primer, wherein the second sequence is palindromic to the first sequence. In one embodiment, the contacting further comprises linking said first single stranded nucleotide and said second single stranded nucleotide, thereby creating a double stranded deoxyribonucleic acid sequence. In one embodiment, the double stranded deoxyribonucleic acid sequence comprises the asymmetric nucleotide barcode sequence. In one embodiment, the linking comprises primer extension. In one embodiment, the primer extension comprises a reverse transcriptase. In one embodiment, the method further comprises amplifying said asymmetric nucleotide barcode sequence, thereby forming amplicons. In one embodiment, the method further comprises sequencing said amplicons, thereby identifying said ligated first and second unique nucleotide barcode sequences. In one embodiment, the method further comprises constructing an intracellular component contact map by determining juxtaposed intracellular components from said identified ligated first and second unique nucleotide barcode sequences. In one embodiment, the contact map comprises a heat map.

In one embodiment, the present invention contemplates a method, comprising: a) providing; i) a first single stranded nucleotide strand comprising a 3' forked end, wherein said 3' forked end comprises a first linker molecule; ii) a second single stranded nucleotide strand comprising a 5' forked end, wherein said second strand is complementary to said first strand; and iii) a binding partner comprising a second linker molecule, wherein said second linker molecule is capable of conjugating with said first linker molecule; b) contacting said binding partner with said first single stranded nucleotide strand under conditions such that said first linker molecule conjugates with said second linker molecule; and c) hybridizing said second strand with said first strand. In one embodiment, the first linker molecule comprises 5-HyNic. In one embodiment, the second linker molecule comprises S-4FB.

In one embodiment, the present invention contemplates a method, comprising: a) providing; i) a first single stranded nucleotide strand comprising a 3' forked end, wherein said 3' forked end comprises a first linker molecule; ii) a second single stranded nucleotide strand comprising a 5' forked end, wherein said second strand is complementary to said first strand; and iii) a binding partner comprising a second linker molecule, wherein said second linker molecule is capable of conjugating with said first linker molecule; c) hybridizing said second strand with said first strand to create a forked adapter molecule; and b) contacting said forked adapter molecule with said binding partner under conditions such that said first linker molecule conjugates with said second linker molecule. In one embodiment, the first linker molecule comprises 5-HyNic. In one embodiment, the second linker molecule comprises S-4FB.

In one embodiment, the present invention contemplates a kit, comprising: a) a first container comprising a plurality binding partners, wherein each said binding partner is attached to a different forked adapter molecule; b) a second container comprising a solution capable of fixing a biological sample; c) a third container comprising buffers and reagents capable of supporting binding of said binding partner to intracellular components of said fixed biological sample; and d) instructions describing how to identify said intracellular components bound to said binding partners. In one embodiment, the forked adapter molecule comprises a unique nucleotide barcode sequence. In one embodiment, the binding partners are selected from the group consisting of antibodies, locked nucleic acids, intracellular receptors, and small organic molecules. In one embodiment, the instructions describe construction of an intracellular component contact map. In one embodiment, the contact map comprises a heat map.

DEFINITIONS

The term "binding partner" as used herein, refers to any molecule having a specific affinity for a particular intracellular component. Such molecules include, but are not limited to, antibodies, locked nucleic acids, receptors, biological cells, derivatized beads, or small organic molecules. Alternatively, a binding partner may also include, a targeting partner as presently understood in the art.

The term "locked nucleic acid" as used herein, refers to any bicyclic nucleic acid where a ribonucleoside is linked between the 2'-oxygen and the 4'-carbon atoms with a methylene unit.

The term "forked adapter molecule" as used herein, refers to any duplex nucleic acid having a first and second strand, wherein the strands encode a unique nucleic acid barcode sequence. The first strand comprising a 3' forked end capable of conjugation with a binding partner. As such, the second strand comprises a 5' forked end that is complementary to the first strand.

The term "unique nucleic acid barcode sequence" as used herein, refers to a specific nucleic acid sequence encoded within a forked adapter molecule capable of providing an unambiguous identification of a specific intracellular component.

The term "linker molecule" as used herein, refers to any organic compound comprising a plurality of reactive sites, wherein a first reactive site is capable of conjugation with either a forked adapter sequence or a binding partner and a second reactive site is capable of conjugation with another linker molecule.

The term "asymmetric nucleotide barcode sequence" as used herein, refers to a joining (i.e., for example, by ligation) of two unique nucleotide barcode sequences. Sequencing of the asymmetric nucleotide barcode sequence provides information related to the proximal location of specific intracellular components.

The term "intracellular component" as used herein, refers to any biological structure in contact with the cytoplasm of a cell. For example, such components may comprise, proteins, enzymes, lipids, nucleic acids, riboproteins, or carbohydrates. Further, these components may represent intracellular organelles including, but not limited to, Golgi bodies, endoplasmic reticulum, nuclear material, ribosomes, mitochondria etc.

The term "close proximity" as used herein, refers to a distance between two intracellular components wherein an interaction between the two components would be expected. Such a distance may range between approximately 0.5 nm-100 nm. Preferably, such a distance may range between approximately 5-50 nm. More preferably, such a distance may range between approximately 10-30 nm. Most preferably, such a distance may range between approximately 15-20 nm.

The term "contact map" as used herein, refers to any presentation of intracellular component organization as defined by spatial proximity. Such contact maps represent a spatio-functional status of a cell based upon the current physiological and/or biochemical state as reflected by the presence of asymmetric nucleotide barcode amplicons. For example, one representation of a contact map is a heat map that presents a visual representation of an array of sequenced asymmetric nucleotide barcodes. The physiological and/or biochemical state of cell may be altered by, for example, changes in cell cycle statue, changes in temperature, changes in pH, drug exposure, toxin exposure. Any change in the physiological and/or biochemical state of a cell would be expected to change the contact map as determined by changes in the identified asymmetric nucleotide barcode amplicon concentrations.

The term "heatmap", as used herein, refers to any graphical representation of data where the values taken by a variable in a two-dimensional map are represented as colors. Heat maps have been widely used to represent the level of mRNA expression of many genes across a number of comparable samples (e.g. cells in different states, samples from different patients) as obtained from DNA microarrays.

The term "attached" as used herein, refers to any interaction between a medium or carrier and a drug. Attachment may be reversible or irreversible. Such attachment includes, but is not limited to, covalent bonding, ionic bonding, Van der Waals forces or friction, and the like.

The term "medium" as used herein, refers to any material, or combination of materials, which serve as a carrier or vehicle for delivering of a drug to an intracellular component. For all practical purposes, therefore, the term "medium" is considered synonymous with the term "carrier".

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering" a drug or compound, as used herein, refers to any method of providing a drug or compound to a biological cell or tissue such that the drug or compound has its intended effect on the biological cell or tissue. Such biological cells or tissues may be derived from a patient.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an compound that has a high affinity for a receptor will provide greater efficacy in preventing the receptor from interacting with its natural ligands, than a compound with a low affinity.

The term "derived from" as used herein, refers to the source of a compound (i.e., for example, a drug or toxin) or sequence (i.e., for example, amino acid or nucleic acid). In one respect, a compound or sequence may be derived from an organism or particular species. In another respect, a compound or sequence may be derived from a larger complex or sequence.

The term "protein" as used herein, refers to any of numerous naturally occurring extremely complex substances that consist of amino acid residues joined by peptide bonds, contain the elements carbon, hydrogen, nitrogen, oxygen, usually sulfur (i.e., for example, binding ligands, hormones, enzymes, antibodies, intracellular structural components). In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "functionally equivalent codon", as used herein, refers to different codons that encode the same amino acid. This phenomenon is often referred to as "degeneracy" of the genetic code. For example, six different codons encode the amino acid arginine.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "biologically active" refers to any molecule having structural, regulatory or biochemical functions.

The term "immunologically active" defines the capability of a natural, recombinant or synthetic peptide, or any oligopeptide thereof, to induce a specific immune response in appropriate animals or cells and/or to bind with specific antibodies.

The term "antigenic determinant" as used herein refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridizing", "hybridize", "hybridization", "annealing", or "anneal" are used interchangeably in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the melting temperature ($T_m$) of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence (i.e., for example, amplicons) and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "self-complementary sequence" refers to a first nucleic acid sequence on a first oligonucleotide, wherein a second oligonucleotide comprises a second nucleic acid sequence in reverse order of the first nucleic acid. In this manner, the first and second nucleic acid sequences are complementary and may hybridize, thereby annealing the first and second oligonucleotides.

As used herein, the term "ligate", "ligating" or "ligation" refers to any method or composition wherein two different double stranded nucleotides have been joined into a single oligonucleotide strand by achemic. Usually, a ligase enzyme facilitates the joining process.

As used herein, the term "linking" or "linked" refers to any method or composition wherein two different molecules have been joined by a chemical reaction and/or enzymatic activity.

As used herein, the term "primer extension" refers to any method wherein two different oligonucleotides become linked by an overlap of their respective terminal complementary primer sequences (i.e., for example, a 3' terminus). Such linking can be followed by an ezymatic extension of both termini using the other oligonucleotide as a templeate. The ezymatic extension may be performed by enzymes including, but not limited to, DNA-dependent DNA polymerases and/or reverse transcriptases.

As used herein, the term "probe" comprises an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

The terms "5' ends" and "3' ends" as used herein, refer to the termini of oligonucleotides because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in adjacent to the coding region of the gene, if needed, to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. Transcriptional control signals in eukaryotes comprise "promoter" and "enhancer" elements. Promoters and enhancers consist of short arrays of DNA sequences that interact specifically with cellular proteins involved in transcription. Maniatis, T. et al., Science 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest. The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: Molecular Cloning: A Laboratory Manual, 2nd ed., Cold Spring Harbor laboratory Press, New York (1989) pp. 16.7-16.8. A commonly used splice donor and acceptor site is the splice junction from the 16S RNA of SV40.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: Molecular Cloning: A Laboratory Manual, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonuclotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "binding" as used herein, refers to any interaction between at least two compounds. Binding may be reversible or irreversible. Such binding may be, but is not limited to, non-covalent binding, covalent bonding, ionic bonding, Van de Waal forces or friction, and the like.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1 illustrates one embodiment of the invention.

FIG. 2A: An asymmetric nucleotide barcode sequence capable of amplification using standard Illumina primers.

FIG. 2B: A symmetric nucleotide barcode sequence forming a hairpin wherein amplification is suppressed.

FIG. 2C: An unligated unique nucleotide barcode sequence that cannot be amplified.

FIG. 20A: 5-Me-Bz-C LNA
FIG. 20B: Bz-A LNA
FIG. 20C: dmf-G LNA
FIG. 20D: T LNA

DETAILED DESCRIPTION

Figure 1A:
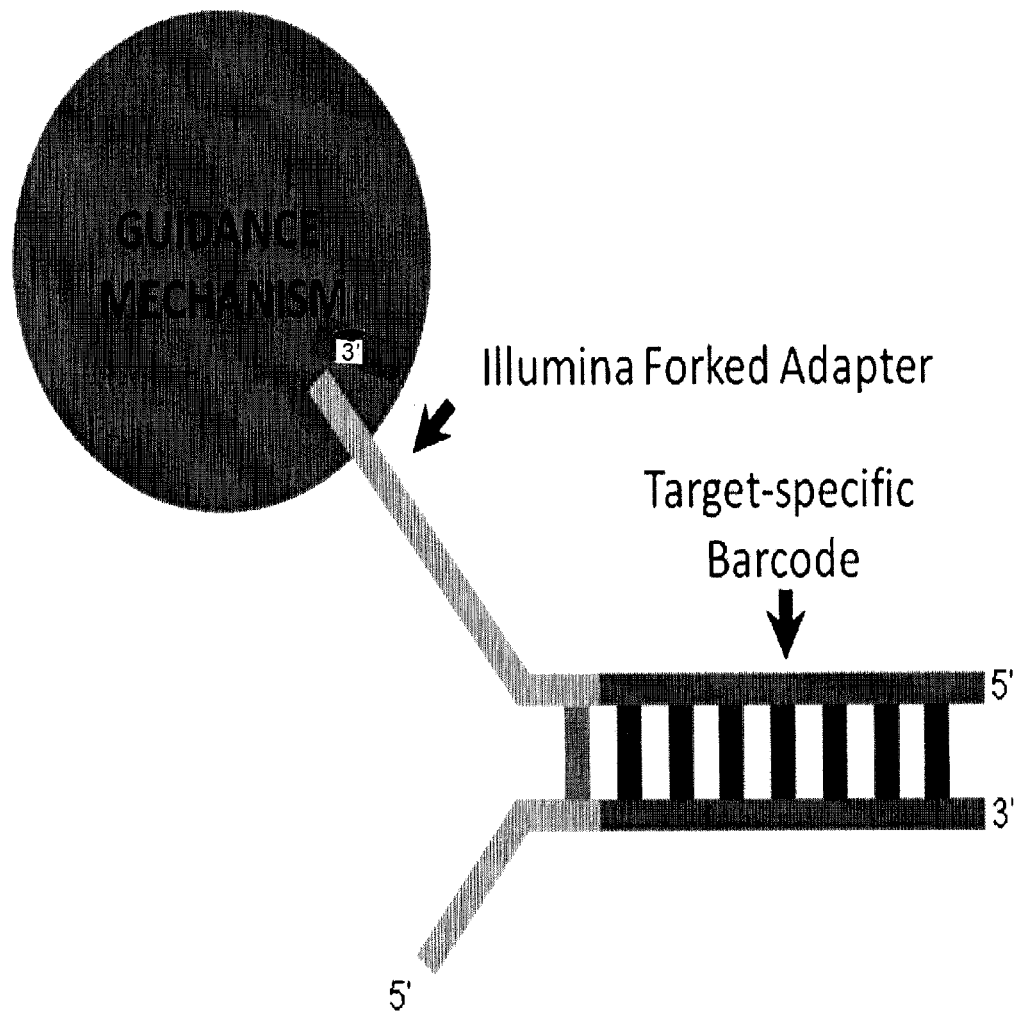
FIG. 1A: A SNAPPLE probe comprising a binding partner including, but not limited, to an antibody or a locked nucleic acid (LNA) linked to a forked adapter molecule having a unique nucleotide barcode sequence.

The present invention is related to the field of intracellular biochemistry. For example, the spatial proximity of intracellular components may be related to their ability to cooperate in intracellular biochemical reactions. In some embodiments, the present invention contemplates a variety of nucleic acid barcoded binding partners capable of determining the spatial proximity of intracellular components as determined by ligation of their respective nucleotide barcodes. As such, an intracellular component contact map may be constructed to fingerprint specific physiological and/or pharmacological intracellular conditions.

I. Protein Proximity Detection by DNA Ligation

The use of nucleotide barcodes have been used to identify proteins. For example, one method is termed proximity ligation. This method utilizes a nucleotide affinity probe having two recognition sites for a target molecule (i.e., a protein), followed by amplification to provide a detection signal. Fredriksson et al., "Protein detection DNA using proximity-dependent ligation assays" *Nature Biotechnology* 20:473-477 (2002). A homodimer of the platelet-derived growth factor B-chain (PDGF-BB), was recently studied. DNA aptamers were used as affinity probes that were obtained through a process of in vitro selection for affinity to PDGF-BB. The selected DNA aptamers were extended with additional nucleotide sequence elements at either the 5' or the 3' end, forming a proximity probe pair. Green et al., "Inhibitory DNA ligands to platelet-derived growth factor B-chain" *Biochemistry* 45:14413-14424 (1996). When two of these probes bind to the same PDGF-BB molecule, their respective sequence extensions hybridize together provided a connector oligonucleotide has been added. This connector oligonucleotide facilitates an enzymatic DNA ligation of the two sequence extensions. The ligation products can then be replicated by nucleic acid amplification through PCR, while unreacted probes remain silent. In summary, this protocol uses two DNA aptamers to identify and localize a single protein. This in vitro DNA amplification technique is applicable to the acquisition of genomic expression information for detection of specific proteins, and not the interaction of a first protein with a second protein having zeptomolar sensitivity (i.e., $40 \times 10^{-21}$ mol).

Other proximity ligation-based protein detection procedures may detect a protein complex via unique nucleic-acid identifiers and subsequent quantification by real-time PCR. Fredriksson et al., "Multiplexed protein detection by proximity ligation for cancer biomarker validation" Nature Methods 4:327-329 (2007). This technology (multiplexed proximity ligation) uses a pair of proximity probes, wherein each probe is composed of an antibody linked to an oligonucleotide, wherein both antibodies have affinity for the same protein. Once both antibodies are bound to the protein, a connecting oligonucleotide is then hybridized to the linked nucleotide of both probes. This provides an "oligonucleotide bridge" that enables an enzymatic ligation joining the 3' end of the first probe with the 5'-end of the second probe. This ligation forms a unique target reporter amplicon containing a specific molecular barcode. Hardenbol et al., *Nat. Biotechnol.* 21:673-678 (2003). These molecular barcodes serve as primer sites, of which some are universal for all protein analytes, whereas others are target-specific. The amplicons are analyzed by real-time PCR thereby generating quantitative protein-abundance data. The assay reporter signal is dependent on a proximal and dual recognition of each target analyte. These assays use high concentrations of proximity probes to promote target binding and ensure a wide dynamic range while maintaining low levels of background ligation events. The background noise in proximity ligation is derived from two main sources: first, proximity probes nonspecifically binding to each other, and second, the connector oligonucleotide binding to two freely diffusing probes, enabling ligation. In general, the workflow of multiplexed proximity ligation assays conceptually resembles that of cDNA synthesis, but for targeted proteins only.

Adaptations of proximity ligation methods having fluorescence based detection methods, have examined the subcellular localization of protein-protein interactions (proximity ligation in situ assay; P-LISA). In one approach, proximity probes having oligonucleotides attached to antibodies were targeted to two different proteins. The first probe's oligonucleotide has a tag sequence that is complementary to a fluorescent oligonucleotide and a primer sequence. The second probe is nonpriming due to a blocking 2'-O-methyl RNA derivative partner. When brought into close proximity, the juxtaposed probe oligonucleotides are stabilized by hybridizing to a connector oligonucleotide, wherein the connector oligonucleotide forms a circular DNA strand. The DNA circle, in turn, serves as a template for localized rolling-circle amplification (RCA) that generates amplicons of the first probe's oligonucleotide tag sequence. When the first probe oligonucleotide tag amplicons are hybridized with a fluorescent oligonucleotide, the intracellular location of the interacting protein pair may be visualized as colored spots. This method has been used to verify protein-protein interactions between endogenous Myc and Max oncogenic transcription factors in response to interferon-c (IFN-c) signaling and low-molecular-weight inhibitors. Soderberg et al., "Direct observation of individual endogenous protein complexes in situ by proximity ligation" *Nature Methods* 3:995-1000 (2006). The oligonucleotides on these P-LISA proximity probes, when brought into close proximity by binding adjacent proteins, serve as templates for the circularization of so-called connector oligonucleotides by enzymatic ligation. The circularized DNA strands remain hybridized to the proximity probes. Upon addition of a phi29 DNA polymerase, the oligonucleotide of the first proximity probe serves as a primer for the RCA reaction, during which the process releases the second probe's oligonucleotide from the DNA circle and is not amplified. The second probe's oligonucleotide cannot serve as a primer because this sequence has three mismatched, exonuclease-resistant 2'-O-methyl RNA nucleotides at the 3' end, which blocks polymerase activity. Consequently, the RCA reaction (~1 hour) generates a randomly coiled, single-stranded product complementary to the first probe's oligonucleotide, while the DNA circle is covalently linked to the antibody-antigen complex. Baner et al., "Signal amplification of padlock probes by rolling circle replication" *Nucleic Acids Res.* 26:5073-5078 (1998). This adduct product is then detected through hybridization of a fluorescence-labeled oligonucleotide that is complementary to a tag sequence in the RCA product. While it is possible to increase the number of proximity probes used in P-LISA to create larger circular amplifiable ligation products to study multiprotein complexes, this method is not useful to simultaneously detect and compare different multiprotein complexes. In particular, P-LISA is not capable of generating an intracellular contact map, based upon simultaneous detection of hundreds, if not thousands, of interacting cell components (i.e., for example, proteins). This limitation is because P-LISA is dependent upon fluorescent detection signals for quantitation of assay results. On the other hand, the unique structure and method of using the presently disclosed SNAPPLE probes allow isolation and sequencing of amplicons that differentiate between hundreds, if not thousands, of interacting cell components.

Although it is not necessary to understand the mechanism of an invention, it is believed that by varying the size and shape of binding partners (i.e., for example, full length intact antibodies or Fab fragments) and/or unique nucleotide barcode sequences on SNAPPLE probes, the methods herein can be used as a molecular ruler, thereby allowing measurements of distances between binding regions. For example, an average distance between binding regions may be approximately 30 nm, (i.e., for example, the size of the two antibodies and a unique nucleotide barcode length). However, longer distances may also be envisioned. Further, shorter distances could be used to improve resolution by limiting detection distances to just over 10 nm.

II. Sequencing-Mediated Numerical Analysis of Parallel Proximity Ligation Events In one embodiment, the present invention contemplates a method termed Sequencing-Mediated Numerical Analysis of Parallel Proximity Ligation Events (SNAPPLE). Although it is not necessary to understand the mechanism of an invention, it is believed that SNAPPLE represents one sequencing-based technique for identifying intracellular components that are in proximity to one another. In one embodiment, the SNAPPLE method further comprises high throughput analyses. For example, tens of thousands of proteins, DNAs, RNAs, and small molecules can be individually and simultaneously probed in a single sequencing run. Such a method results in an intracellular component interaction contact map, yielding qualitative and quantitative data about all inter-component proximity relations.

In one embodiment, the present invention contemplates a composition comprising a SNAPPLE probe. In one embodiment, the probe comprises a binding partner, capable of specific interaction with an intracellular component. In one embodiment, the binding partner includes, but is not limited to, an antibody, LNA, DNA, a binding ligand, a receptor, a derivatized bead, a biological cell, or a chemical partner (i.e., a small organic molecule). In one embodiment, the probe further comprises a forked oligonucleotide adapter molecule. In one embodiment, the forked adapter molecule comprises a component-specific oligonucleotide barcode. See, FIG. 1A.

Figure 1B:
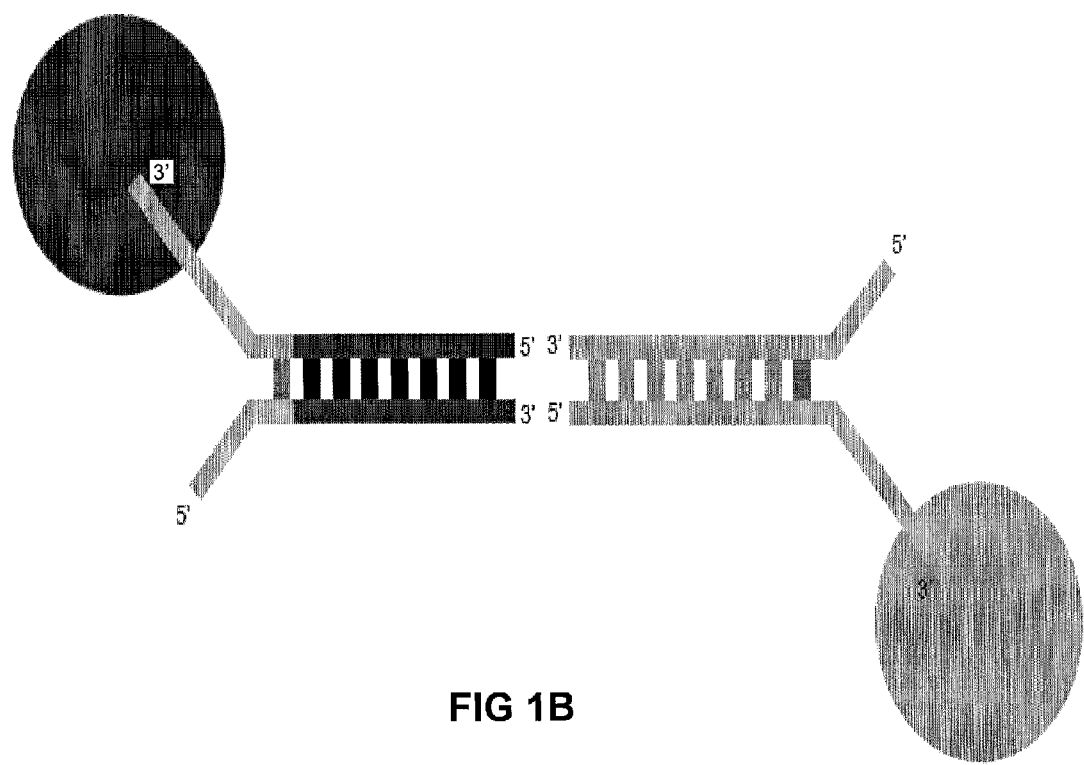
FIG. 1B: Juxtaposition of two SNAPPLE probes in a sample, wherein the corresponding unique nucleotide barcode sequences are brought into close proximity
Figure 1C:
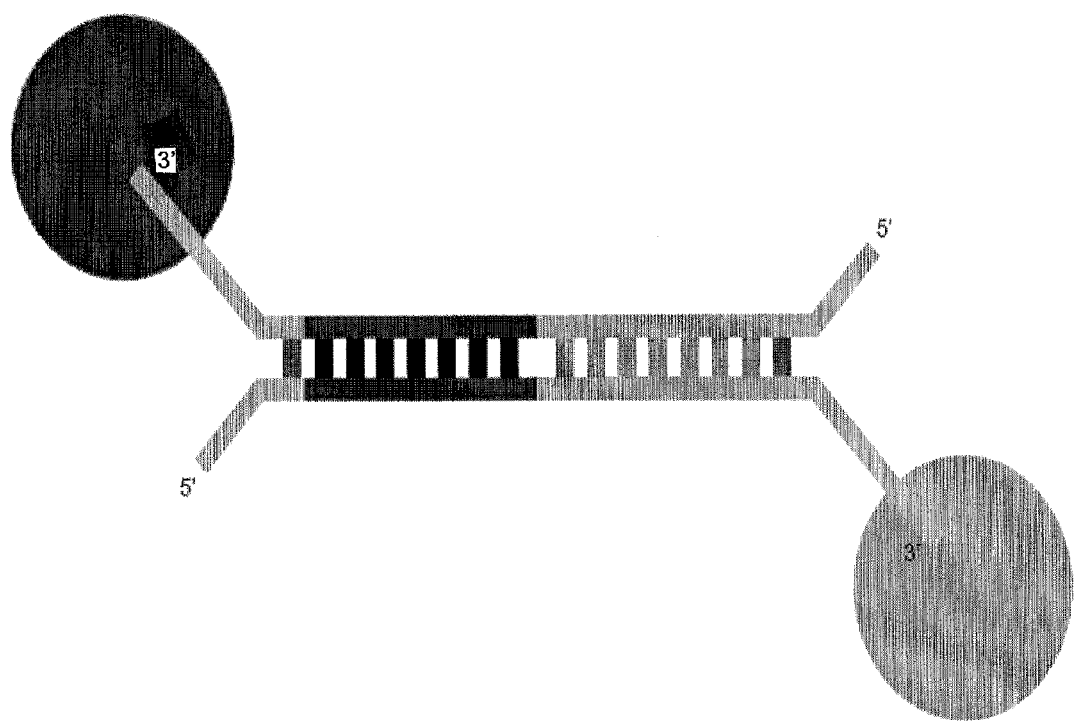
FIG. 1C: Ligation of the unique nucleotide barcode sequences between two juxtaposed probes to form an asymmetric nucleotide barcode sequence.
Figure 2:
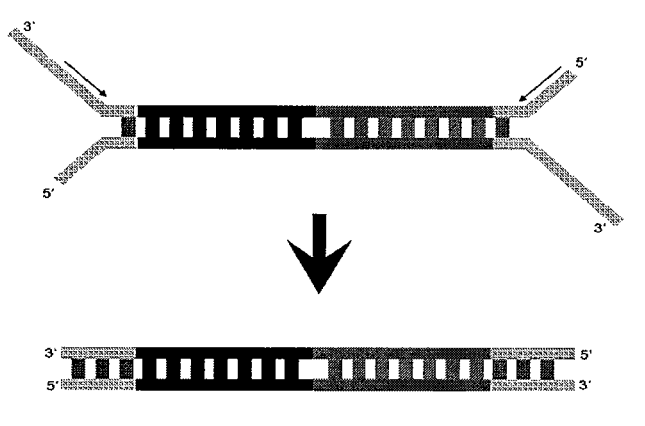
FIG. 2 illustrates one embodiment of the invention.
Figure 2:
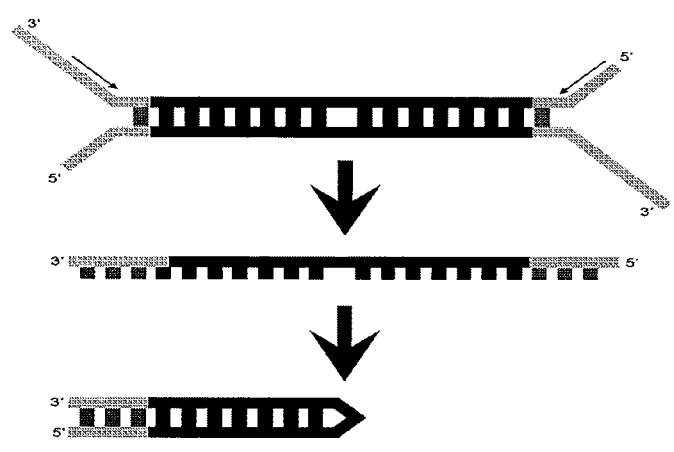
Figure 2:
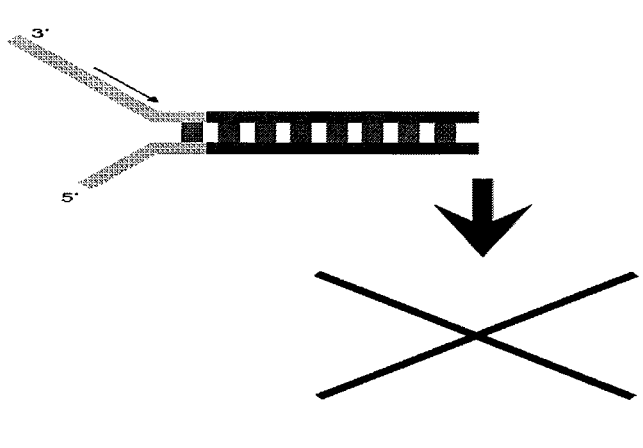
Figure 3:
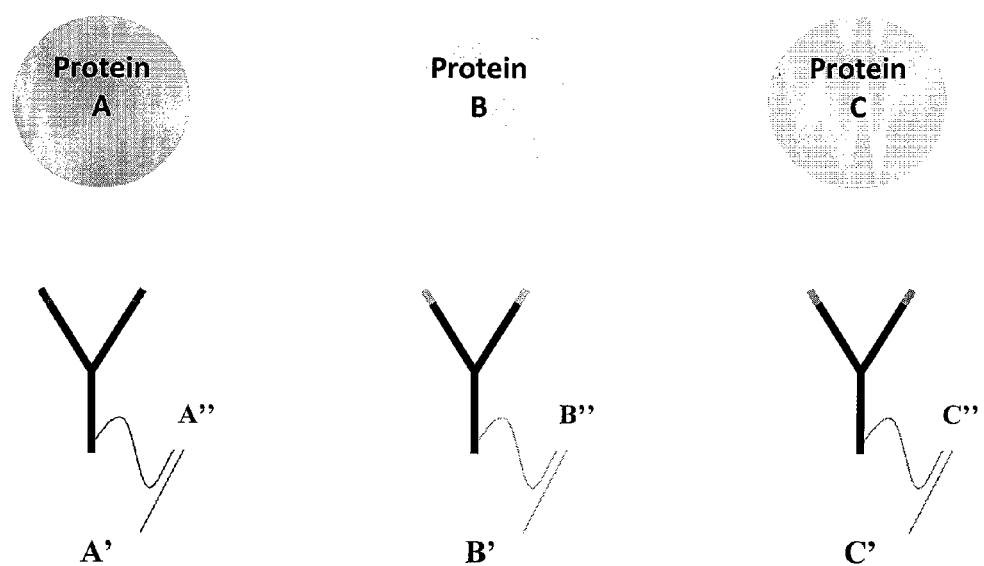
FIG. 3 illustrates three possible embodiments of SNAPPLE probes wherein each probe (e.g., A', B', and C') has specific affinity to a unique intracellular component (e.g., Protein A, Protein B, and Protein C) and each probe is conjugated to a unique nucleotide barcode sequence (e.g. A", B", and C").

In one embodiment, the present invention contemplates a SNAPPLE method comprising a) contacting a sample with a fixative; b) incubating the fixed sample with a plurality of SNAPPLE probes; and c) blunt-end ligating the probes. Although it is not necessary to understand the mechanism of an invention, it is believed that when two different probes bind to their respective components that are spatially colocated, the corresponding forked oligonucleotide adapter molecules may be ligated, thereby forming a junction comprising an asymmetric nucleotide barcode (i.e., wherein the junction comprises two different unique nucleotide barcodes derived from two different SNAPPLE probes). See, FIG. 1B and FIG. 1C. In one embodiment, the method further comprises amplifying each asymmetric nucleotide barcode with a different single primer pair. See, FIG. 2A. Although it is not necessary to understand the mechanism of an invention, it is believed that unligated adapters will not be amplified and symmetric junctions lead to large hairpins that suppress amplification. See, FIG. 2B and FIG. 2C, respectively. In one embodiment, the method further comprises sequencing the amplicons in, for example, an Illumina flowcell, to identify the unique nucleotide barcodes that were ligated together. In one embodiment, the sequencing data creates a 'contact map' identifying paired intracellular components (i.e., for example, those intracellular components that were in close proximity). As such, many different binding partners may be used together provided each binding partner is conjugated to a unique nucleotide barcode sequence (i.e., thereby forming a different SNAPPLE probe). For example, three different proteins (i.e., for example, Protein A, Protein B, and Protein C) may be assayed simultaneously because each protein has a specific affinity for one of three different binding partners (i.e., for example, antibody A', antibody B', and antibody C') wherein each binding partner is conjugated to a unique nucleic acid barcode sequence (i.e., for example, sequence A", sequence B", and sequence C"). See, FIG. 3.

Figure 4:
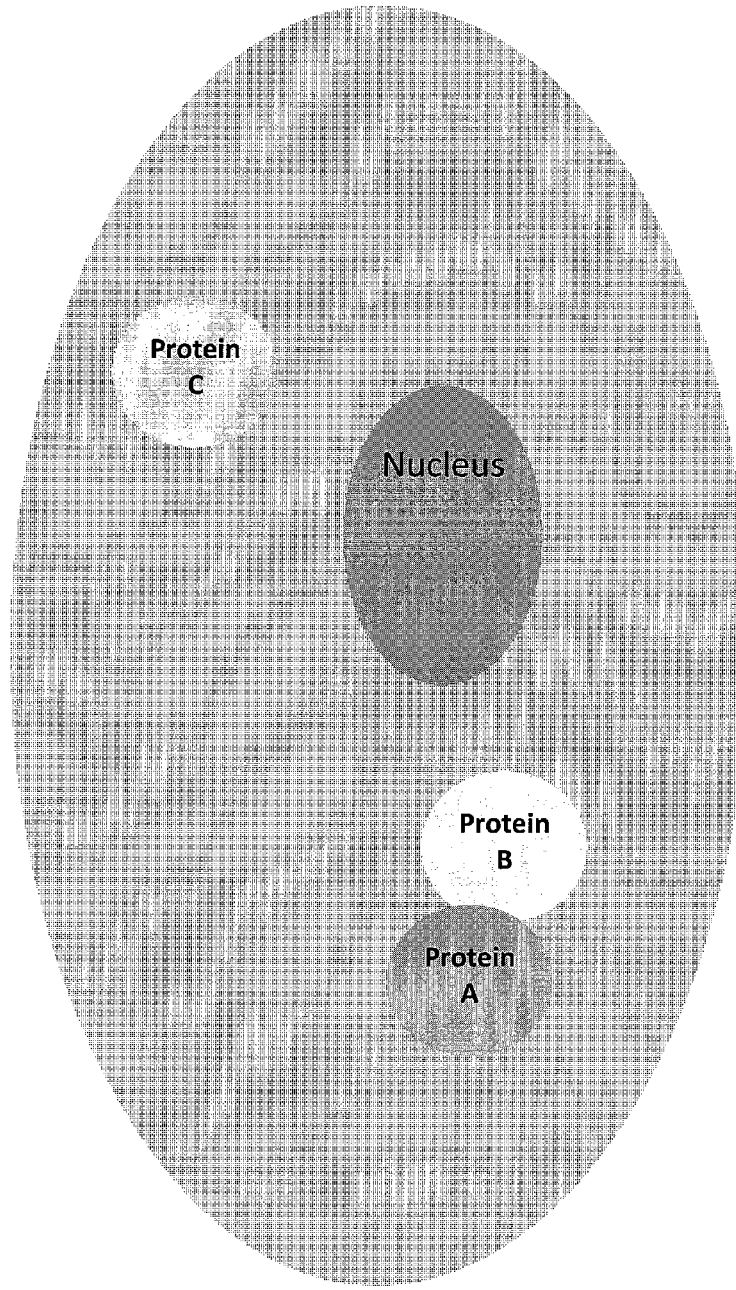
FIG. 4 illustrates the spatial localization of representative intracellular components of FIG. 3, following a fixation step.
Figure 5:
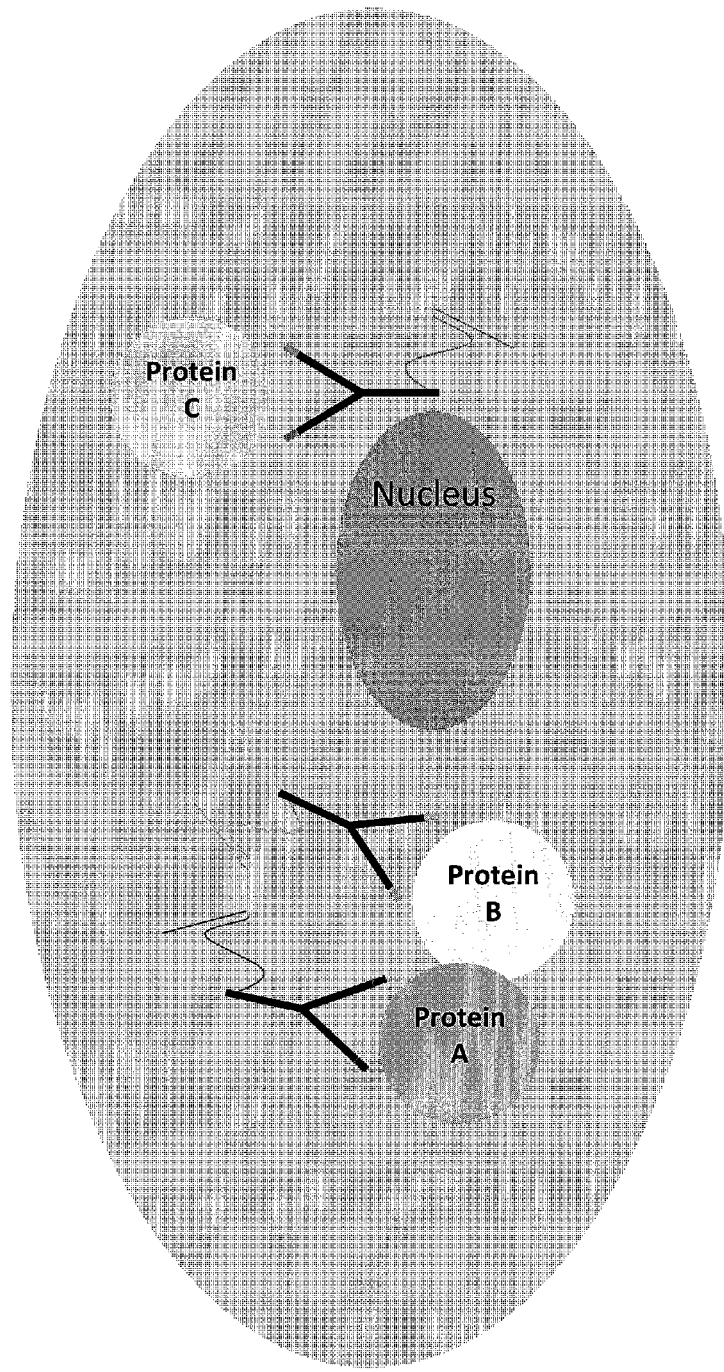
FIG. 5 illustrates the binding of the SNAPPLE probes to the fixed intracellular components of FIG. 4. Note the close proximity of SNAPPLE probe A' and B' binding to co-located Protein A and Protein B, respectively.
Figure 6:
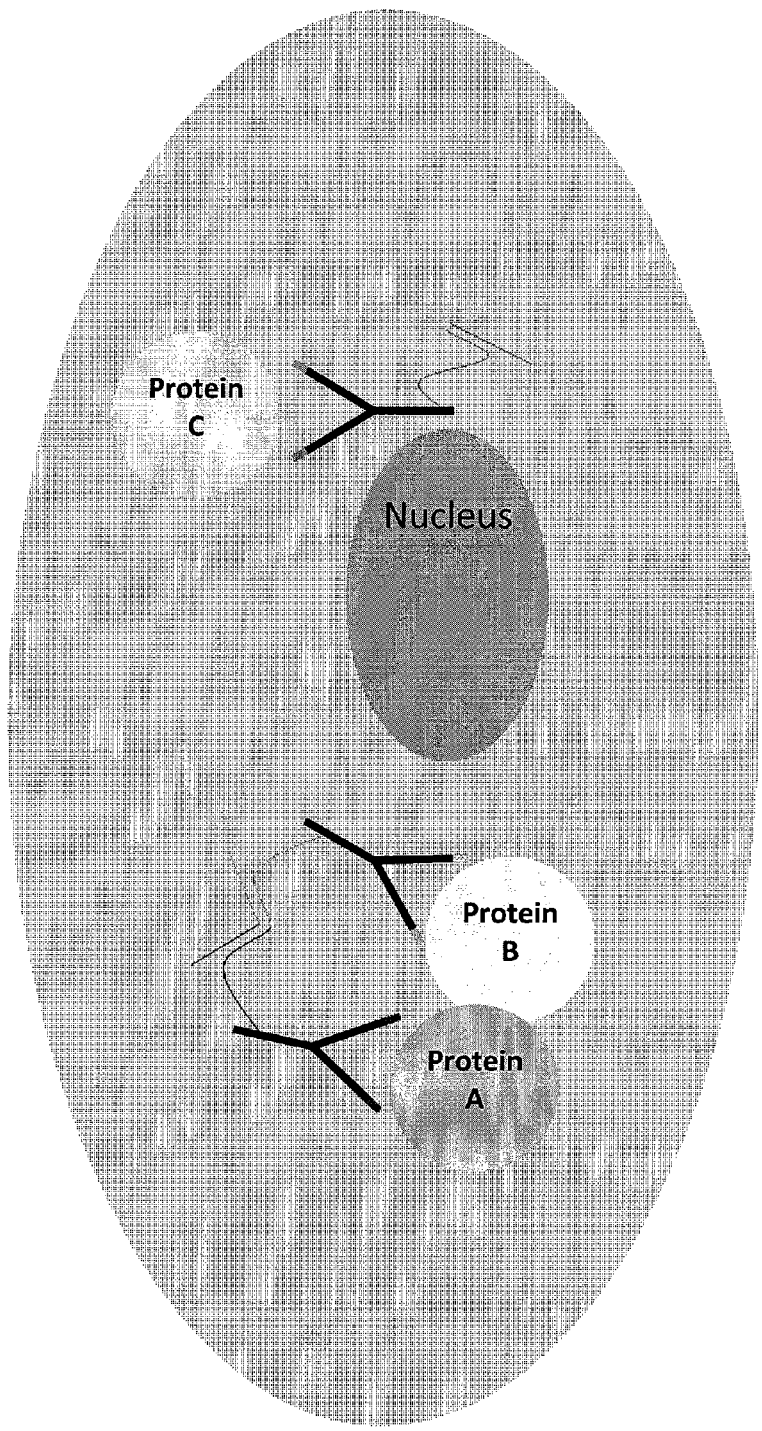
FIG. 6 illustrates the blunt end ligation of the unique nucleotide barcodes of the SNAPPLE probes after attachment to their respective intracellular components. Note that, in this case, an asymmetric nucleotide barcode sequence is formed as a junction between the two proximal SNAPPLE probes attached to Protein A and Protein B.
Figure 7:
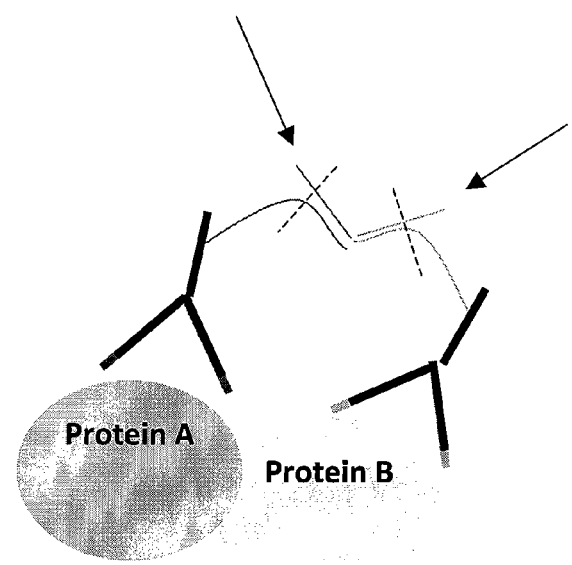
FIG. 7 illustrates one embodiment of two ligated SNAPPLE probes comprising an asymmetric nucleic acid barcode sequence (area between dashed lines). Arrows: Forked end adapter.

Briefly, the SNAPPLE method comprises a fixation step that immobilizes such representative proteins A & B in relation to their intracellular spatial localization that may reflect their biochemical functions. See, FIG. 4. The SNAPPLE method further comprises an incubation step, wherein the SNAPPLE probes are introduced into the intracellular space under conditions such that they bind and/or attach to specific intracellular components. In some situations, at least two SNAPPLE probes attach within close proximity. See, FIG. 5. The SNAPPLE method further comprises a ligation step, wherein the unique nucleotide barcodes on the juxtaposed SNAPPLE probes are contacted with a ligase enzyme, thereby resulting in an asymmetric barcode sequence by blunt end ligation. See, FIG. 6. The SNAPPLE method further comprises washing, amplification, and isolation of the ligated SNAPPLE probes comprising an asymmetric barcode sequence. See, FIG. 7. The resulting configuration of the asymmetric barcode sequence demonstrates the advantages of the "forked adaptor" design, such that after ligation, the two original barcodes display an unattached fork and an attached fork that facilitate attachment of the primers in preparation for sequencing (see arrows).

A specific disadvantage of extant proximity ligation methods only allow a single probe to ligate to a single partner probe. While the above described 'multiplex' protein quantification method (i.e., Fredriksson et al.) can utilize multiple probes, each probe is limited to ligate only to a single partner probe. Secondly, multiplex techniques requires that each probe have two distinct binding sites for the target molecule, thereby increasing the formation of homodimeric ligations. These techniques do not suggest designing probes such that any probe may ligate with any other probe with equal efficiency and still be able to read out the results via conventional nucleic acid sequencing analysis (i.e., for example, qPCR mediated sequencing).

For example, unlike multiplex proximity ligation techniques, some embodiments presented herein allow performance of qPCR after designing a set of N probes specific to N targets such that each oligo tag (i.e., for example, a first UNB) can ligate to any and every other oligo tag (i.e., for example, a second, third, fourth, etc., UNB). Even when two different short dsDNA's are conjugated to different probes and blunt end ligated together, problems arise during conventional qPCR. If all the probe dsDNA's hybridize to the same upstream primer A, then PCR fails to generate amplicons because the resulting products will become hairpins, due to primer complemetarity at the single stranded cDNA strand ends. One the other hand, if each probe dsDNA sequence hybridizes to a different primer (i.e., primer A and primer B), the ligated dsDNAs can be amplified with a mixture of primer A and primer B. This technique, however, requires twice as many probes and a much more complicated protocol generating many ligation products between A-A primed ligated dsDNAs and B-B primed ligated dsDNAs (i.e., homodimeric ligation dsDNAs). The dsDNAs having identical primers at each end do not respond efficiently to PCR, thereby decreasing amplicon yield. It is believed that these disadvantages cannot be eliminated by using ssDNA, overhangs, or linker oligos, which many of the proximity ligation protocols advocate. Although it is not necessary to understand the mechanism of an invention, it is believed that for efficient qPCR of any heterodimeric ligated dsDNA the use of ssDNA, overhangs, or linker oligos generates an unacceptable amount of contaminating homodimeric PCR product artifacts as opposed to heterodimeric PCR products of interest.

In one embodiment, the present invention contemplates a forked oligonucleotide sequence (i.e., for example, a forked adapter molecule) that is conjugated to a probe (i.e., for example, a binding partner) which is believed to overcome the homodimer qPCR problems described above. Although it is not necessary to understand the mechanism of an invention, it is believed that by using a forked adapter molecule primer A/primer B, qPCR may be performed without the need for two probes per target, thereby vastly reducing the formation of homodimer PCR products. It is also believed that the hairpin PCR products that do form from homodimer PCR products, facilitate sequencing analysis because they suppress same probe-same probe ligation product frequency.

A. Intracellular Component Complexes

In one embodiment, the present invention contemplates a pair of SNAPPLE probes that are respectively linked to different antibodies, wherein each antibody comprises a specific affinity to an intracellular component (i.e., for example, intracellular proteins). Although it is not necessary to understand the mechanism of an invention, it is believed that if the two intracellular components tend to form a complex, the proximal binding of the corresponding antibody-SNAPPLE probe pair places the conjugated barcoded adapters into close proximity. It is further believed that this proximity facilitates ligation of the unique nucleotide barcodes, thereby creating a join specific to the juxtaposed component pair (i.e., for example, an asymmetric ligated barcode). Thus, when the asymmetric ligated barcode is amplified, the amplified products comprise a specific nucleotide sequence that identifies the juxtaposed intracellular components (i.e., for example, an inter-protein complex). Other embodiments contemplate complexation of protein-RNA components or RNA-RNA components that may be identified and analyzed in a similar manner.

B. Nucleic Acid Structure Determination

Figure 19:
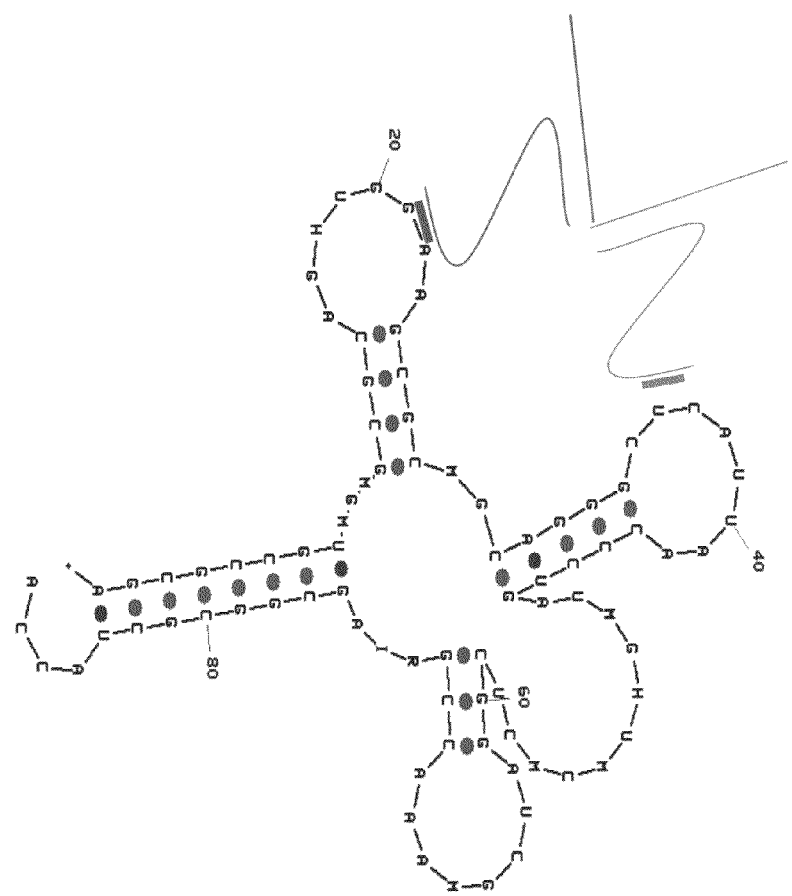
FIG. 19 presents one embodiment of a messenger RNA having multiple SNAPPLE probe binding sites.

In one embodiment, a SNAPPLE probe comprises a plurality of binding partners, wherein the moieties attach to different regions on the same intracellular component (i.e., for example, folded DNA or mRNA). See, FIG. 19. Although it is not necessary to understand the mechanism of an invention, it is believed that these multi-targeted probes can be used to approximately determine intracellular component folds or three-dimensional (i.e., for example, tertiary or quaternary) structures of an in vivo intracellular component. In one embodiment, the intracellular component comprises a protein having multiple conformations. In one embodiment, a multiple conformational protein comprises a prion.

Such nucleic acid structure determinations may be accomplished by SNAPPLE probes comprising binding partners selected from commercially available chromatin-immunprecipitating antibodies (NimbleGen), for example:

1. Core Histones & Modifications
    Histone H2A Abcam ab18255
    Histone H2B Abcam ab1790
    Histone H3 Abcam ab1791 17277777, 15231737, 17220878, 17559302
    Histone H4 Abcam ab7311
    Histone H3 (me1-K4) Abcam ab8895 17277777, 17559302
    Histone H3 (me2-K4) Upstate 07-030 17277777, 16980610, 15988478, 17559302
    Histone H3 (me3-K4) Abcam ab8580 16604156, 17344414
    Histone H3 (me1-K9) Abcam ab9045 15923188
    Histone H3 (me3-K9) Abcam ab 1186 16751344, 17542650, 17604720
    Histone H4 (me1-K20) Abcam ab9051 17512414
    Histone H4 (me2-K20) Abcam ab1409 12397363
    Histone H4 (me3-K20) Abcam ab9053 17512414
    Histone H3 (me3-Lys27) Upstate 07-449 16751344, 16618801, 15231737, 17542650, 17339329, 17604720
    Histone H3 (me1-K36) Abcam ab9048 17512414
    Histone H3 (me3-K36) Abcam ab9050 16122420
    Histone H3 (me1-K79) Abcam ab2886 17512414
    Histone H3 (me2-K79) Abcam ab3594 17512414
    Histone H3 (me3-K79) Abcam ab2621 16122420
    Histone H4 (acetyl K5) Abcam ab1758 15292231
    Histone H4 (acetyl K8) Abcam ab1760 15292231
    Histone H4 (acetyl K12) Abcam ab1761
    Histone H4 (acetyl K16) Abcam ab1762
    Histone H4 (acetyl K5/8/12/16) Upstate 06-866 17277777, 17218097, 16980610, 17229572, 16914732, 17559302
    Histone H3 (acetyl K9/14) Upstate 06-599 15988478, 17559302, 16473879, 16980610
2. Transcription Factors
    AP-2α Santa Cruz sc-184X 17053090
    AP-4 Santa Cruz sc-18595X 12391156
    ATF-2 Santa Cruz sc-6233X 15226416
    C/EBPβ Santa Cruz sc-150X 16914732
    c-fos Santa Cruz sc-52X 14672732
    c-jun Upstate 06-225 14764426
    c-myb Santa Cruz sc-7874X 12377807
    c-myc Santa Cruz sc-764X 16606705, 17568006
    CREB Upstate 06-863 15194748
    E2F1 (KH20/KH95) Upstate 05-379 17053090, 16606705
    ERα Upstate 06-935 12897156
    FOXA1 Abcam ab5089 15743813
    GATA-1 Santa Cruz sc-265X 15456760
    GR Santa Cruz sc-1004X 16914732
    HIF1α Abcam ab2185
    HNF-3γ Santa Cruz sc-5361X 15358835
    HNF-4α Santa Cruz sc-8987X 12416993
    HSF1 Stressgen SPA-901 14673135
    Max Santa Cruz sc-765X 15226411
    NF-kappaB p50 Upstate 06-886 12783888
    NF-kappaB p65 Santa Cruz sc-8008X 14527995
    Oct-3/4 Santa Cruz sc-8628X 17567999, 16751344
    p53 Santa Cruz sc-6243X 15205322
    RXR Santa Cruz sc-774X 16497728, 17229572, 16914732
    Sp1 Upstate 07-124 15180995

Sp3 Upstate 07-107 15180995
Stat2 Santa Cruz sc-476X 14600148
Stat3 Santa Cruz sc-482X 14659888
Stat5α Santa Cruz se-1081X 14659888
SUZ12 Abcam ab12201 17542650, 16618801, 15231737, 16751344, 17604720
USF-1 Santa Cruz sc-8983X 15187018
VDR Santa Cruz sc-1008X 16613987, 17229572, 16914732
YY1 Santa Cruz sc-7341X 15326102
3. Chromatin Modifiers
BAF170 Santa Cruz sc-9744X 15314177
Brg-1 Santa Cruz sc-10768X 15314177
Brm Santa Cruz sc-6450X 15314177
CARM1 Upstate 07-080 14764426
CBP Santa Cruz sc-369X 16497728, 17218097
HDAC1 Upstate 06-720 15226416
HDAC2 Santa Cruz sc-7899X 12783888
LSD1 Abcam ab1772
mSin3A Santa Cruz sc-994X 15314177
NCoR Santa Cruz sc-8994X 15226416
p300 Santa Cruz sc-585X 17277777
PCAF Upstate 07-141 14764426
SUV39H1 Abeam ab12405
TRAP220 Santa Cruz sc-5334X 17277777
4. Pre-Initiation Complex
Pol II Santa Cruz sc-899X 16618801, 15231737, 17344414, 16606705
RNAPII, 8WG16 Covance MMS-126R 17277777, 15988478, 17604720
TAFII p250 (6B3) Santa Cruz sc-735X 17277777, 15988478
TFIIB Santa Cruz sc-274X 15247294
TFIID (TBP) Santa Cruz sc-273X 15280358
TFIIF Abcam ab4449
TFIIH p89 Santa Cruz sc-293X 11493692
5. DNA Methylation
5-methylcytidine Eurogentec BI-MECY-0500 16007088, 17128275
Dnmt1 Abcam ab5208 16357870
Dnmt3b Abcam ab2851 16357870
MBD1 Abcam ab3753 14633992
MBD3 Abcam ab3755 14633992
MeCP2 Abcam ab3752 14633992

II. SNAPPLE Probes

Figure 8:
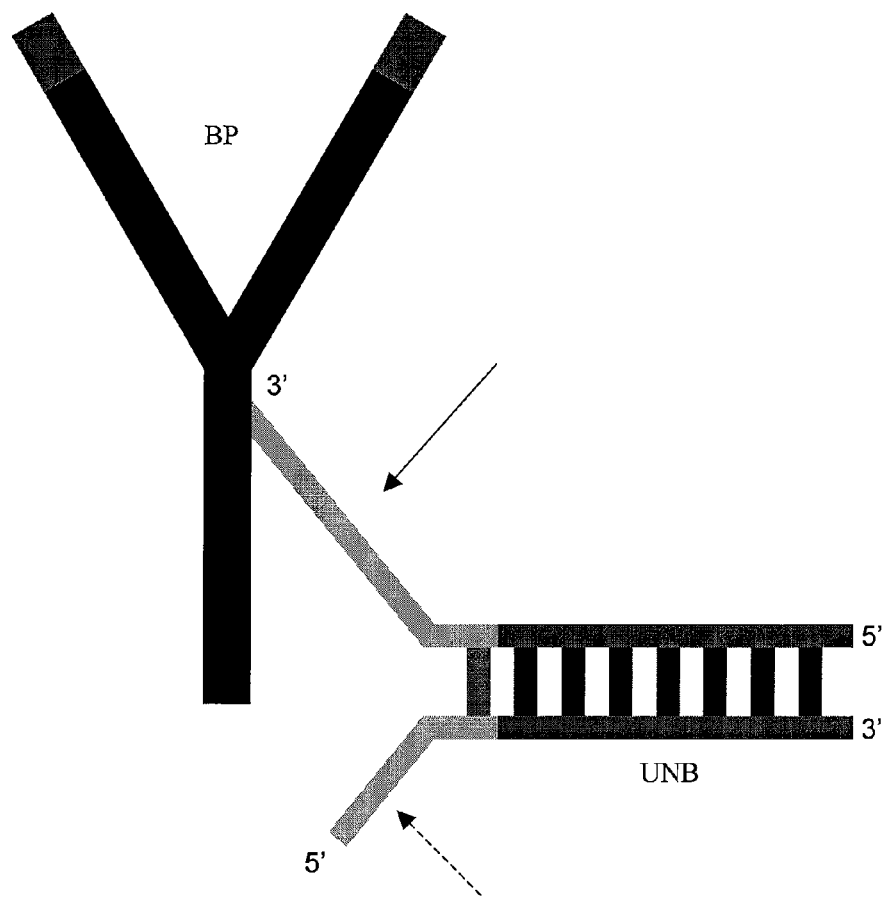
FIG. 8 illustrates one embodiment of a SNAPPLE probe comprising a binding partner (BP) conjugated to a unique nucleotide barcode sequence (UNB) having a forked adaptor configuration. In this illustration, a first end of the forked adapter (solid arrow) is linked to the binding partner, while the second end of the forked adapter (dashed arrow) is free.

In one embodiment, the present invention contemplates a composition comprising a binding partner, wherein the partner is conjugated to a nucleic acid sequence. In one embodiment, the nucleic acid sequence comprises a forked adapter molecule. See, FIG. 8 (arrow). In one embodiment, the forked adapter molecule is conjugated to the binding partner at a 3' end. In one embodiment, the forked adapter molecule comprises a nucleic acid sequence. In one embodiment, the forked adapter sequence comprises a linker molecule.

Figure 9:
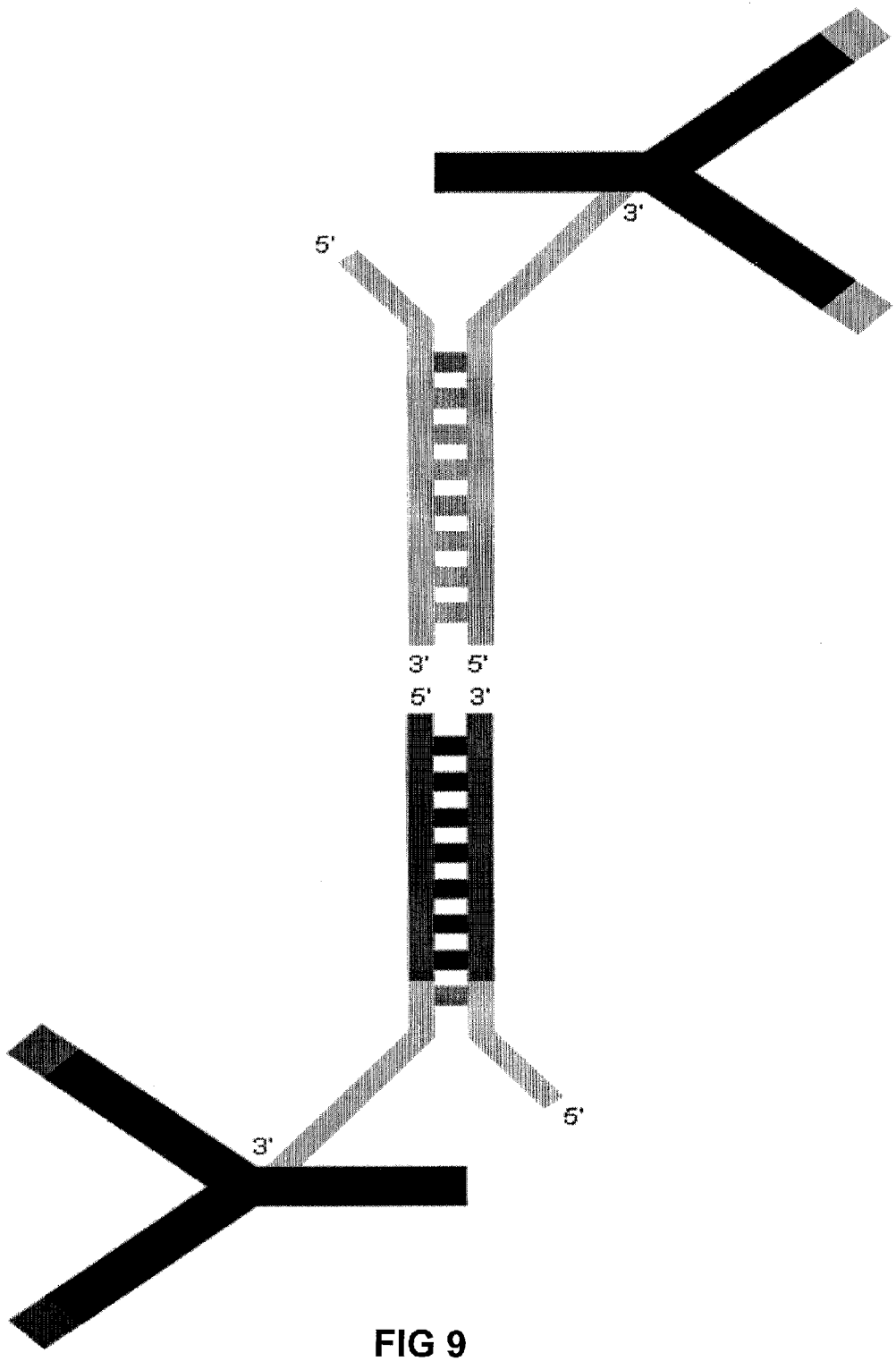
FIG. 9 presents a close up view of one embodiment of a juxtaposition of two UNBs from two different SNAPPLE probes before ligation.
Figure 10:
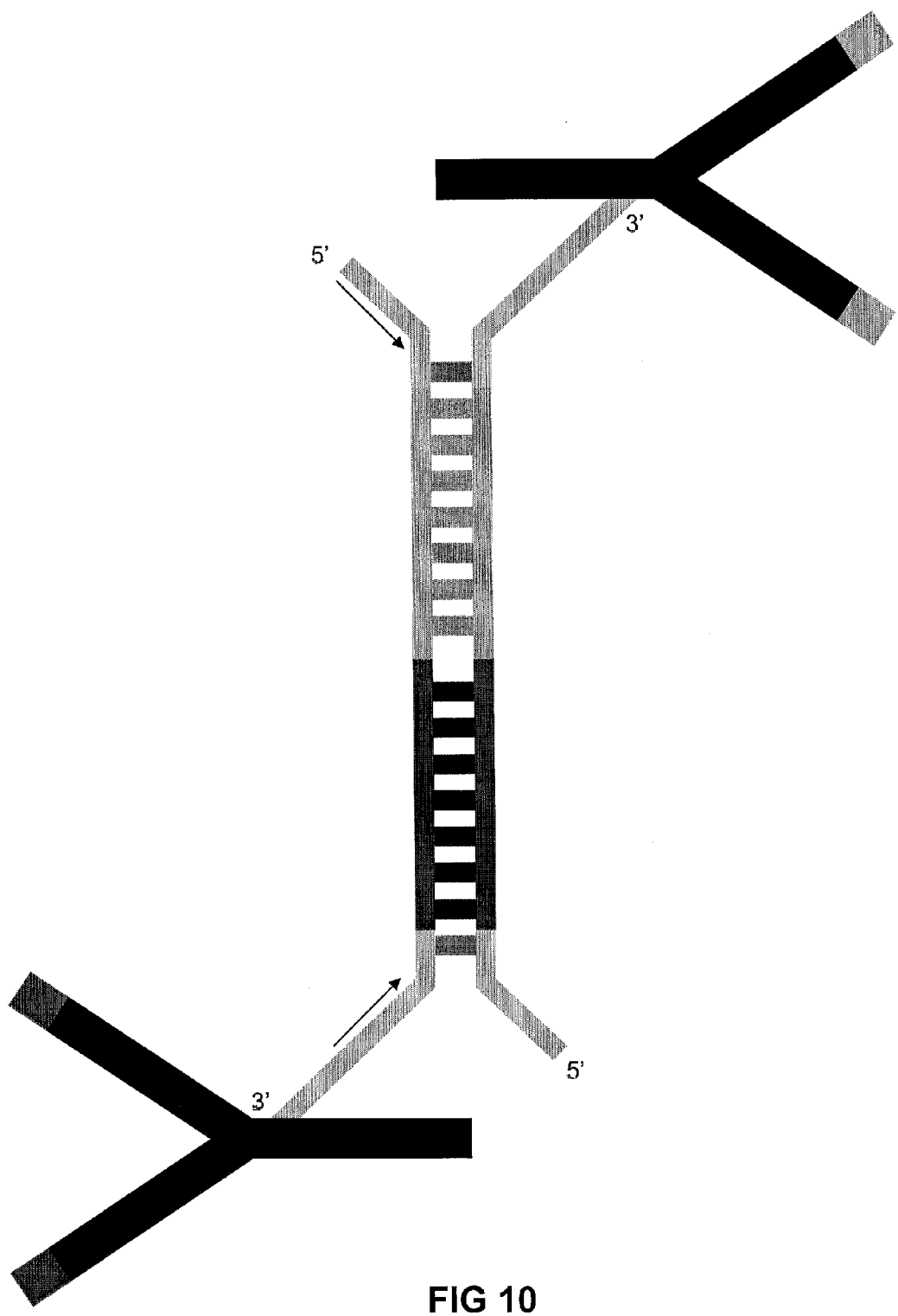
FIG. 10 presents a close up view of one embodiment of a ligated asymmetric nucleotide barcode sequence comprising UNBs from two different SNAPPLE probes, wherein a 3' and 5' primer pair (see arrows) have been hybridized.
Figure 11:
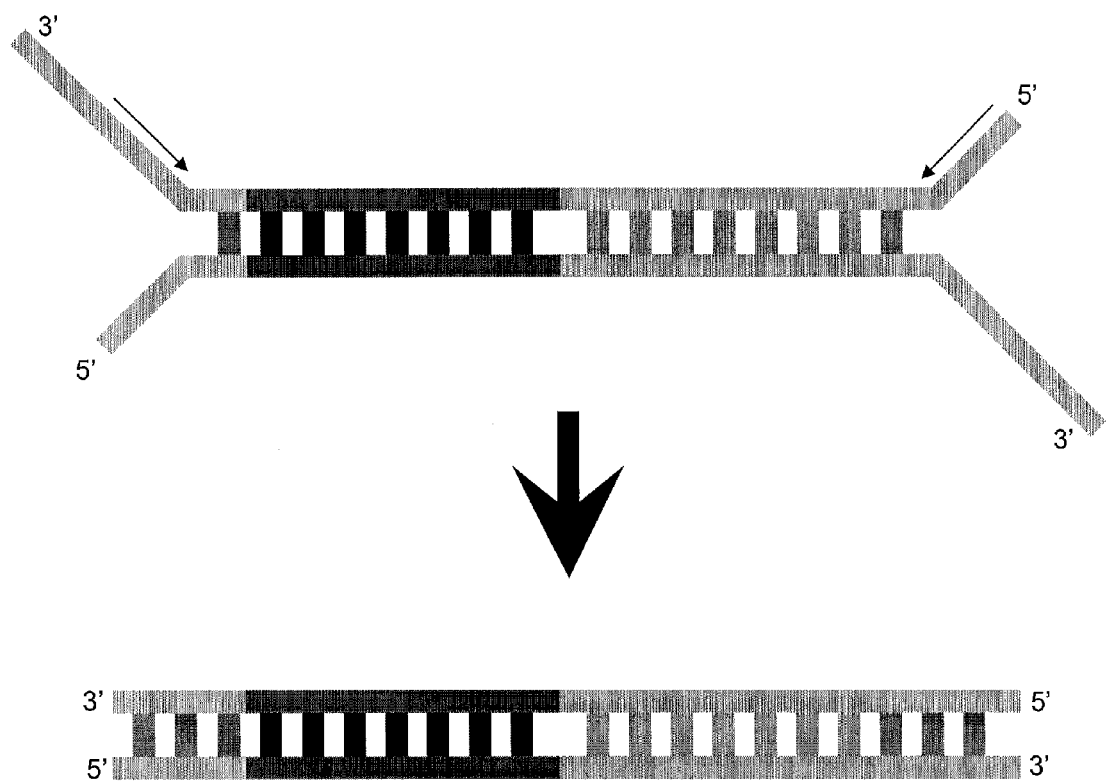
FIG. 11 presents a schematic of the amplification of the ligated asymmetric barcode using a specific primer pair (arrows), thereby resulting in amplicons of the joined UNBs.

In one embodiment, the present invention contemplates a composition comprising two SNAPPLE probes attached by ligation between their respective unique nucleotide barcode sequences (UNBs). Such UNB ligation is facilitated because, after the binding partners are attached to their respective intracellular components, the UNBs are positioned in close proximity. See, FIG. 9. After UNB ligation, specific primers may be hybridized to the 3' and 5' ends of one UNB forked adapter molecule strand. See, FIG. 10 (See arrows). After placement of the primers, quantitative polymerase chain reaction is performed upon the asymmetric barcode sequence to form amplicons. See, FIG. 11. There are many ways to process the amplicon sequence readouts including, but not limited to: i) Illumina sequencing that may be capable of processing an unlimited number of amplicons; ii) microarray hybridizations that may be capable of processing hundreds of amplicons; and iii) Luminex Flow Sorting that may be capable of processing tens of amplicons.

Figure 12:
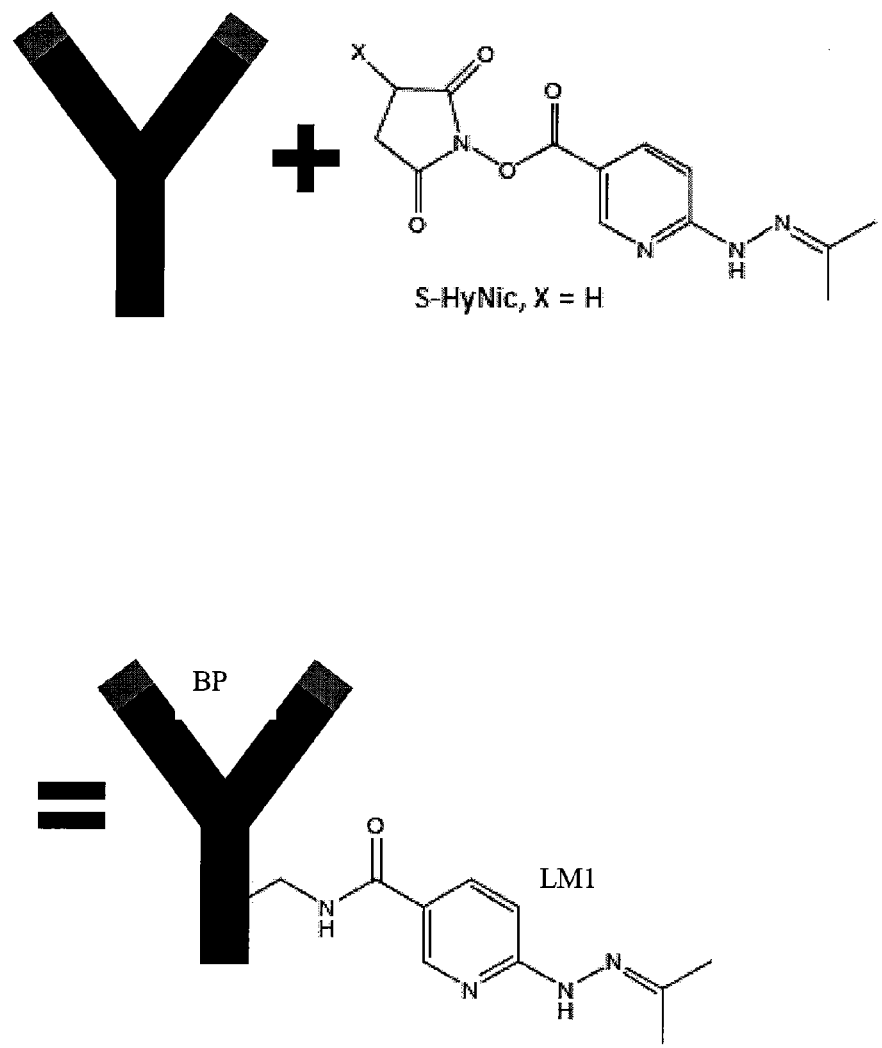
FIG. 12 presents one embodiment for making a SNAPPLE probe by conjugating a first linker molecule (LM1) to a binding partner (BP).

In one embodiment, the present invention contemplates a method for making a SNAPPLE probe comprising: providing a binding partner and a first linker molecule. In one embodiment, the first linker molecule comprises 5-HyNic. In one embodiment, the first linker molecule is conjugated to the binding partner to create a 5-HyNic conjugated binding partner (i.e., for example, an antibody). See, FIG. 12.

Figure 13:
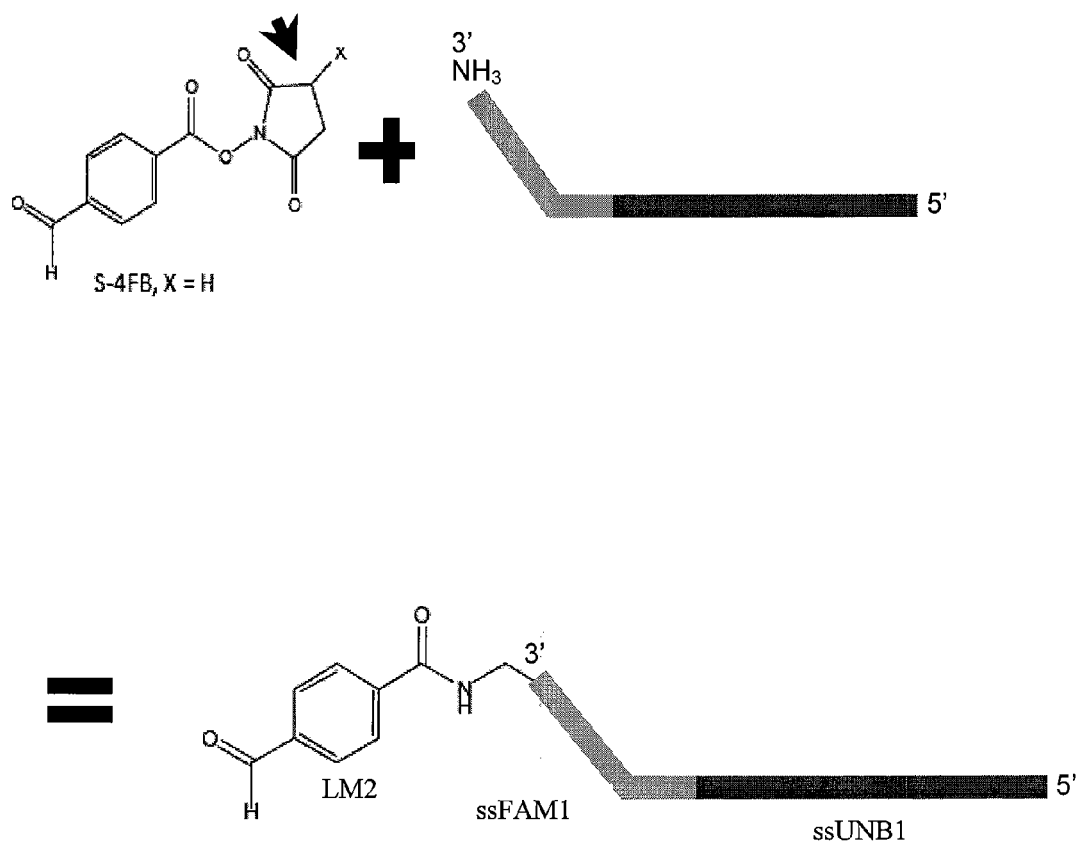
FIG. 13 presents one embodiment for making a SNAPPLE probe by conjugating a second linker molecule (LM2) to a first single stranded forked adapter molecule (ssFAM1) attached to a first single stranded unique nucleotide barcode sequence (ssUNB1).
Figure 14:
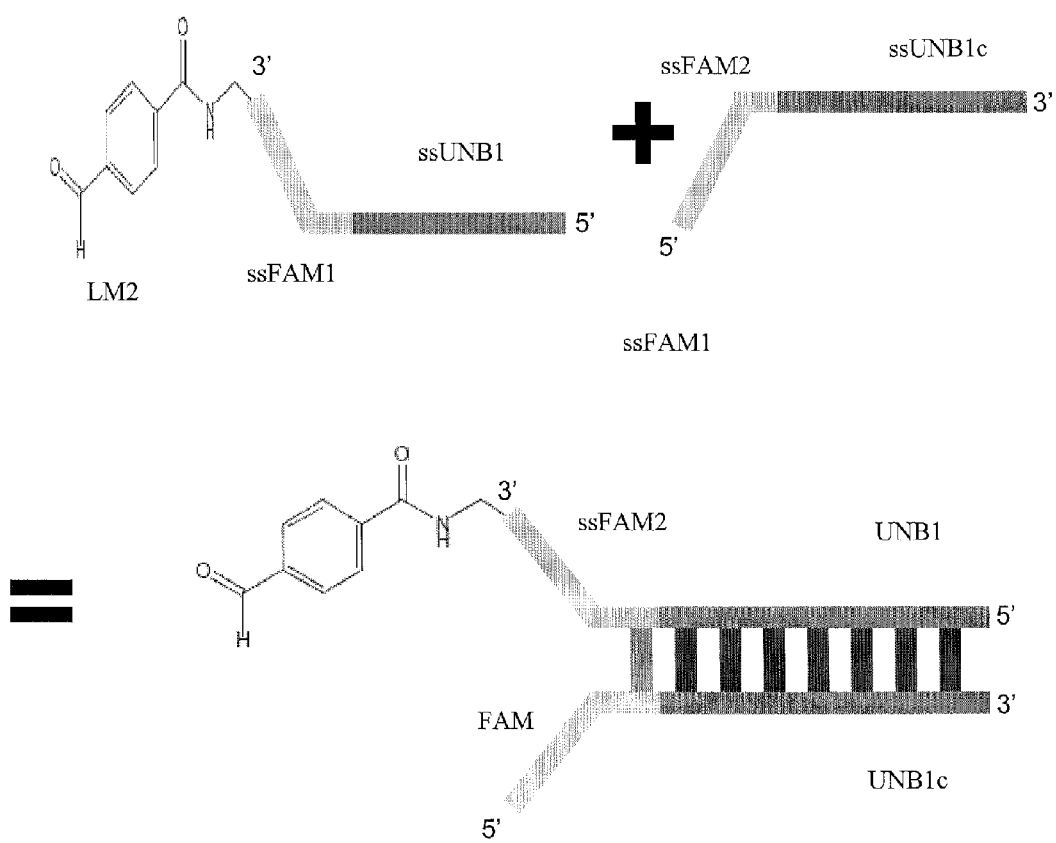
FIG. 14 presents one embodiment for making a SNAPPLE probe by hybridizing a LM2-ssFAM1-ssUNB1 to a second single stranded forked adapter molecule (ssFAM2) having a complementary single stranded unique nucleotide sequence (ssUNB1c) to create a forked adapter molecule (FAM).

In one embodiment, the present invention contemplates a method for making a SNAPPLE probe comprising: providing a first single stranded forked adapter molecule and a second linker molecule. In one embodiment, the second linker molecule comprises S-4FB. In one embodiment, the second linker is conjugated to the forked adapter molecule to create a S-4FB conjugated forked adapter, wherein the adapter is attached to a first single stranded unique nucleotide barcode sequence. See, FIG. 13. In one embodiment, the first single stranded unique nucleotide barcode sequence is annealed with a second single stranded unique nucleotide barcode sequence, wherein the second sequence is complementary to the first sequence. See, FIG. 14.

Figure 15:
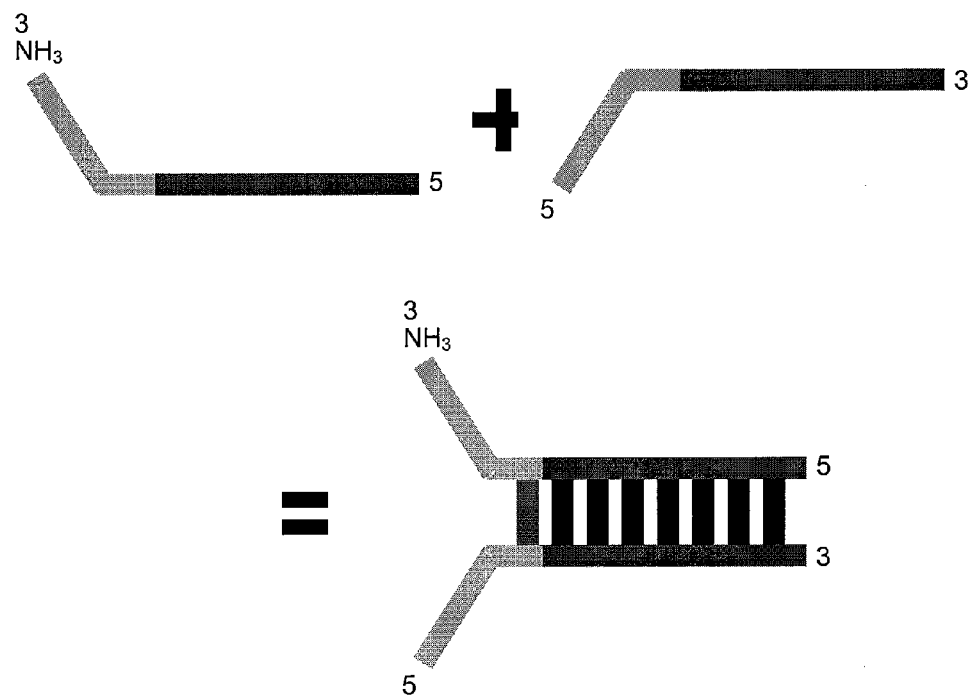
FIG. 15 presents one embodiment for making a SNAPPLE probe by hybridizing an ssFAM1 and an ssFAM1c to form a forked adapter molecule (FAM).
Figure 16:
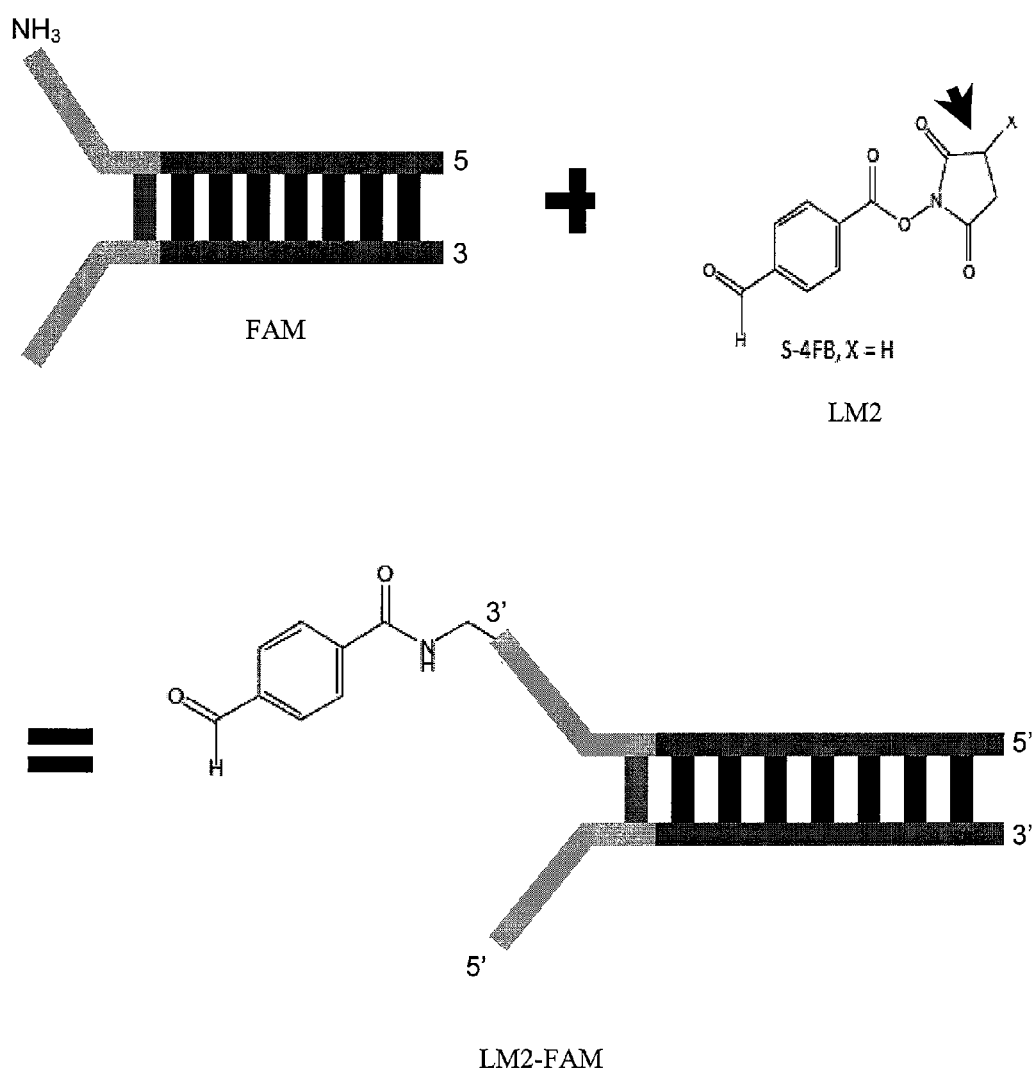
FIG. 16 presents one embodiment for making a SNAPPLE probe by conjugating a second linker partner (LM2) to a forked adapter molecule (FAM) to create an LM2-FAM molecule.

In one embodiment, the present invention contemplates a method for making a SNAPPLE probe comprising: providing a first single stranded forked adapter molecule (ssFAM1) and a complementary first single stranded forked adapter molecule (ssFAM1c). In one embodiment, the method further comprising hybridizing the ssFAM1 and ssFAM1c, thereby forming a forked adapter molecule (FAM). See FIG. 15. In one embodiment, the FAM is conjugated to a second linker molecule (LM2; for example, S-4FB), to create a forked adapter molecule conjugated to a second linker molecule (LM2-FAM). See, FIG. 16.

Figure 17:
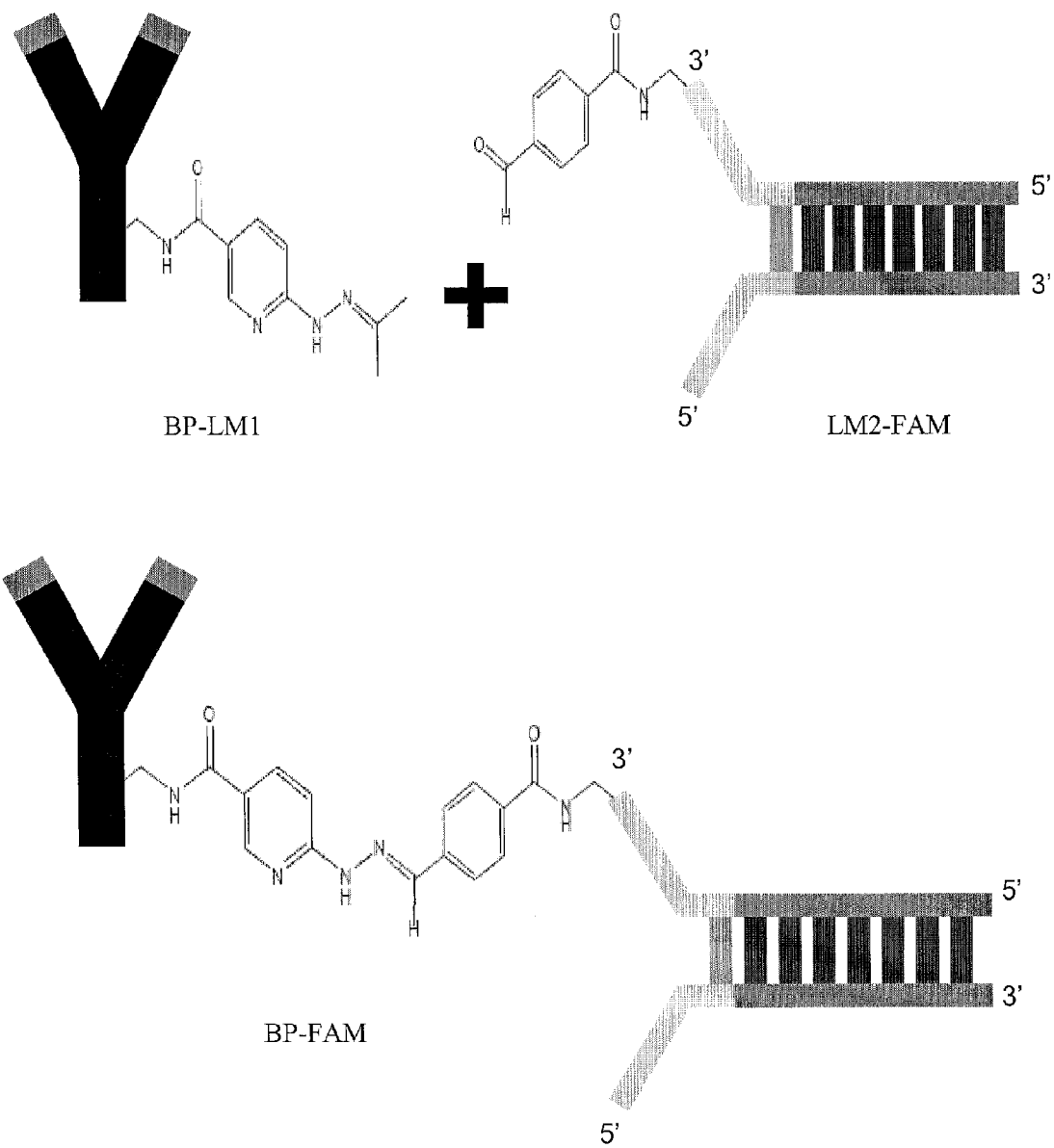
FIG. 17 presents one embodiment for making a SNAPPLE probe by conjugating a binding partner attached to a first linker molecule (BP-LM1) with a forked adapter molecule attached to a second linker molecule (LM2-FAM) to form a binding partner-forked adapter molecule complex (BP-FAM).

In one embodiment, the present invention contemplates a method for making a SNAPPLE probe comprising: providing a binding partner conjugated to a first linker molecule and a forked adapter molecule conjugated to a second linker molecule. In one embodiment, the first and second linker molecules are conjugated to form a binding partner-forked adapter molecule complex (BP-FAM). See, FIG. 17.

A. Antibody Binding Partners

Antibody-based detection systems for specific antigens are useful for various molecular and cellular analyses and/or clinical diagnostics. Such systems are very flexible because antibody specificity can be tailored to particular epitopes. For example, a number of antibody technologies include, but are not limited to, genetic engineering of antibody molecules (M. J. Geisow, *Trends Biotechnol.* 10:75 (1992); production of catalytic antibodies (Lerner et al., *Science* 252:659 (1991).); and bispecific antibodies (Bolhuis et al., *J. Cell. Biochem.* 47:306 (1991). Further enhancement of antigen detection sensitivity should facilitate the specific detection of rare antigens.

Antibody conjugation to oligonucleotides were reported to be useful in quantifying the presence of minute quantities of antigen (i.e., for example, Immuno-PCR). Sano et al., *Science* 258:120-122 (1992). In this early work, a streptavidin-protein A chimera that possesses tight and specific binding affinity both for biotin and immunoglobulin G was used to attach a biotinylated DNA specifically to antigen-monoclonal antibody complexes that had been immobilized on microtiter plate wells. Then, a segment of the attached DNA was amplified by PCR. Analysis of the PCR products by agarose gel electrophoresis after staining with ethidium bromide allowed as few as 580 antigen molecules ($9.6 \times 10^{-22}$ moles) to be readily and reproducibly detected. Direct comparison with enzyme-linked immunosorbent assay with the use of a chimera-alkaline phosphatase conjugate demonstrated an enhancement in detection sensitivity (i.e., for example, approximately $\times 10^5$). Consequently, PCR amplification should improve the sensitivity of any antigen detection system and, in principle, could be applied to the detection of single molecules.

The accuracy of such assays may be increased by using antibodies or DNA aptamers directed to a target protein having multiple epitopes followed by proximity ligation and PCR amplification of the ligation product. Fredriksson et al., *Nature Biotechnology* (2002); and *Nature Methods* (2007). It was speculated that multiple binding sites eliminated non-specific binding by a single antibody. A similar proximity-ligation-based method was developed for localizing a single protein complex using a complex ligation/Rolling Circle Amplification protocol followed by fluorescence microscopy to detect the presence of an encoded tag. Soderberg et. al., *Nature Methods* (2006). Pull-down of genomic targets using DNA may also be performed by related techniques. Dejardin et al., *Cell* (2009).

The development of SNAPPLE probes may be validated using the proteins EGFR, Her-2, and c-Myc. It has been reported that EGFR and Her2 form complexes while EGFR/c and Myc do not form complexes in U2 osteosarcoma cells. Soderberg et. al., *Nature Methods* (2006). Verification that the SNAPPLE biochemistry works may be performed by using: i) an EGFR protein; ii) a Her-2 protein; iii) a c-Myc protein; and iv) at least one other protein. Each protein may, or may not, be conjugated with a His tag and/or a FLAG tag, at the N and C termini, respectively. Monoclonal antibodies are commercially available for both the His and FLAG tags A different unique nucleotide barcode is conjugated to a His monoclonal antibody and a FLAG monoclonal antibody. Each of the tagged proteins, are then individually incubated with the barcoded antibodies. Quantitative polymerase chain reactions (qPCR) may be used to determine yield of His/FLAG SNAPPLE junctions. Chimeric barcodes should be obtained in the presence of a protein, in proportion to the relative proximity of the N and C termini.

Verification that the SNAPPLE biochemistry works may be performed by using: i) EGFR conjugated with a His tag only; ii) EGFR conjugated with a FLAG tag only; and iii) EGFR conjugated with both a His tag and a FLAG tag at the N and C terminii, respectively. Highly specific antibodies for both His and FLAG are commercially available, wherein a first unique nucleotide barcode is conjugated to a His monoclonal antibody (mAb), and a second unique nucleotide barcode is conjugated to a FLAG monoclonal antibody. Next, the three protein samples are individually incubated with each of the two barcoded monoclonal antibodies. Quantitative polymerase chain reaction (qPCR) is then performed on each sample to determine the yield of asymmetric junctions resulting from a ligation of the first barcode and the second barcode. Due to the proximity of the first and second barcodes in the doubly-tagged EGFR, a chimeric barcode comprising the first and second nucleic acid barcodes are formed only with the double-tagged EGFR.

Verification that the SNAPPLE biochemistry can determine proximity of multiple targets in vitro may be performed by using: i) EGFR tagged with a His tag only; ii) Her-2 tagged with a FLAG tag only, and iii) C-Myc tagged with a FLAG tag only. This combination of proteins is useful because EGFR interacts with Her-2, but EGFR does not interact with c-Myc. A first unique nucleotide barcode is conjugated to a His monoclonal antibody, and a second unique nucleotide barcode is conjugated to a FLAG monoclonal antibody. Next, the three proteins are incubated as pairs: i) EGFR+Her-2; ii) EGFR+c-Myc; and iii) Her2+c-Myc. Quantitative polymerase chain reaction (qPCR) is then performed on each sample to determine the yield of asymmetric junctions (i.e., for example, an asymmetric nucleotide barcode sequence or chimeric barcode) resulting from a ligation of the first unique nucleotide barcode and the second unique nucleotide barcode. The asymmetric junctions comprising a chimeric barcode of the first and second nucleic acid barcodes are strongly enriched in the EGFR-Her-2 pair incubation, due to the proximity of the first and second unique nucleotide barcodes.

Verification that the SNAPPLE biochemistry can determine proximity of multiple targets inside a cell may be performed by using: i) EGFR tagged with a His tag only; ii) Her-2 tagged with a FLAG tag only, and iii) C-Myc tagged with a FLAG tag only. This combination of proteins is useful because EGFR interacts with Her-2, but EGFR does not interact with c-Myc. A first unique nucleotide barcode is conjugated to a His monoclonal antibody, and a second unique nucleotide barcode is conjugated to a FLAG monoclonal antibody. Next, three cell populations (i.e., for example, U2 osteosarcoma cells) are transfected with the three possible protein pairs: i) EGFR+Her-2; ii) EGFR+c-Myc; and iii) Her-2+c-Myc. Quantitative polymerase chain reaction (qPCR) is then performed on each sample to determine the yield of asymmetric junctions resulting from a ligation of the first unique barcode and the second unique barcode. The asymmetric junctions comprising a chimeric barcode of the first and second unique nucleotide barcodes are strongly enriched in the EGFR-Her-2 pair transfected cells, due to the proximity of the first and second unique nucleotide barcodes.

Verification that the SNAPPLE biochemistry can determine proximity of multiple targets in vivo may be performed by using: i) EGFR; ii) Her-2; and iii) C-Myc. A first unique nucleotide barcode is conjugated to a EGFR monoclonal antibody. A second unique nucleotide barcode is conjugated to a Her-2 monoclonal antibody. A unique third nucleotide barcode is conjugated to a c-Myc monoclonal antibody. Next, three cell populations (i.e., for example, U2 osteosarcoma cells) are transfected with the three possible protein pairs: i) EGFR+Her-2; ii) EGFR+c-Myc; and iii) Her-2+c-Myc. Quantitative polymerase chain reaction (qPCR) is then performed on each sample to determine the yield of asymmetric junctions resulting from a ligation of the various barcodes. The asymmetric junctions comprising a chimeric barcode of the first and second unique nucleic acid barcodes are strongly enriched in the EGFR-Her-2 pair transfected cells, due to the proximity of the first and second unique nucleotide barcodes.

B. Locked Nucleic Acid (LNA) Binding Partners

Figure 18:
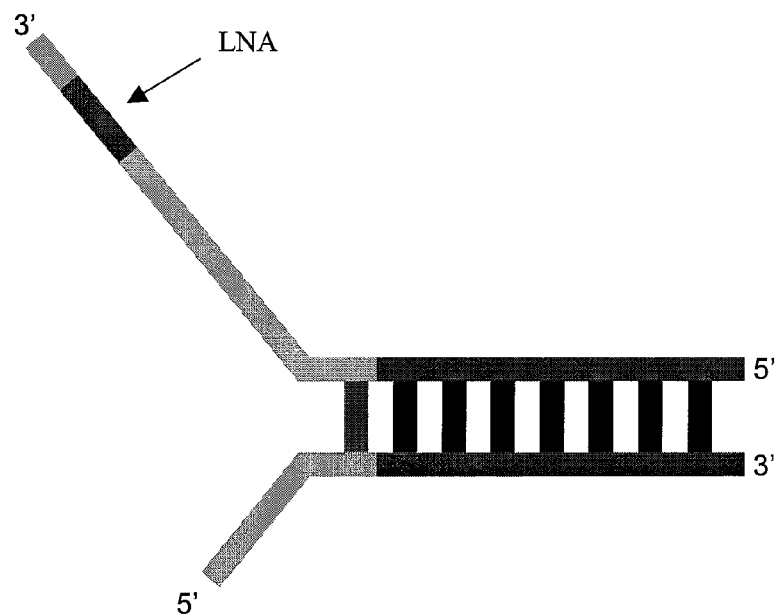
FIG. 18 presents one embodiment of a SNAPPLE probe comprising a locked nucleic acid (LNA) binding partner.

In one embodiment, the present invention contemplates a composition comprising a first single stranded forked adapter sequence, wherein the adapter sequence encodes a binding partner. In one embodiment, the binding partner comprises a locked nucleic acid (LNA) sequence. In one embodiment, the binding partner is attached to a unique nucleotide barcode sequence. See, FIG. 18. Synthetic procedures for locked nucleic acids may be found. Singh et al, *Chem. Comm.* 455-456 (1998); and Wengel J., *Acc. Chem. Res.*, 32:301-310 (1998).

Locked Nucleic Acid (LNA) was first described as a class of conformationally restricted oligonucleotide analogues. The design and ability of oligos containing locked nucleic acids (LNAs) to bind supercoiled, double-stranded plasmid DNA in a sequence-specific manner. The main mechanism for LNA oligos binding plasmid DNA has been demonstrated to be by strand displacement. LNA oligos are more stably bound to plasmid DNA than similar peptide nucleic acid (PNA) 'clamps' for procedures such as particle mediated DNA delivery (gene gun). It was shown that LNA oligos remain associated with plasmid DNA after cationic lipid-mediated transfection into mammalian cells.

LNA oligos can bind to DNA in a sequence-specific manner so that binding does not interfere with plasmid conformation or gene expression. LNA oligonucleotides exhibit thermal stabilities towards complementary DNA and RNA, which allows mismatch discrimination. The high binding affinity of LNA oligos allows for the use of short probes in antisense protocols and LNA is recommended for use in any hybridization assay that requires high specificity and/or reproducibility, e.g., dual labeled probes, in situ hybridization probes, molecular beacons and PCR primers. Furthermore, LNA offers the possibility to adjust $T_m$ values of primers and probes in multiplex assays. Each LNA base addition in an oligo increases the $T_m$, by approximately 8° C. As a result of these significant characteristics, the use of LNA-modified oligos in antisense drug development is now coming under investigation, and recently the therapeutic potential of LNA has been reviewed.

The synthesis and incorporation of LNA bases can be achieved by using standard DNA synthesis chemistry. Detailed research results have not yet concluded as to the amount of LNA bases and regular DNA base combination in successful antisense and gene delivery experiments. Due to the high affinity and thermal stability of the LNA: DNA duplex it is not advised to have more than 15 LNA bases in an oligo; this induces strong self-hybridization.

The use of LNA C base requires special synthesis and post synthesis protocols. LNA-containing oligonucleotides can be purified and analyzed using the same methods employed for standard DNA. LNA can be mixed with DNA and RNA, as well as other nucleic acid analogues, modifiers and labels. LNA oligonucleotides are water soluble, and can be separated by gel electrophoresis and precipitated by ethanol.

Figure 20:
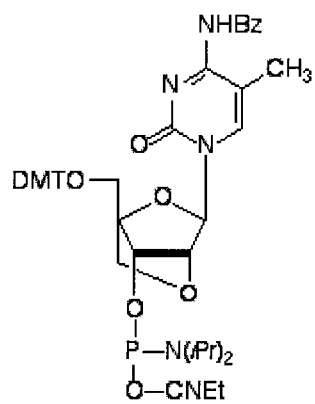
FIG. 20 presents several embodiments of locked nucleic acids.
Figure 20:
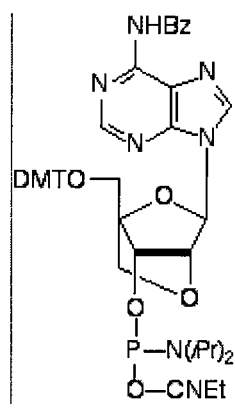
Figure 20:
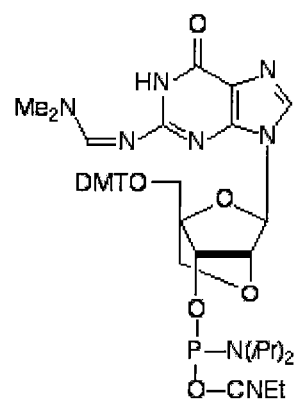
Figure 20:
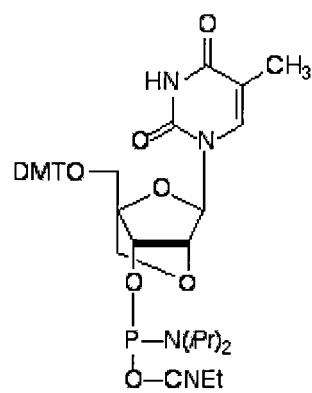

Specific types of locked-nucleic Acid (LNA) phosphoramidites have been reported. U.S. Pat. No. 6,268,490 (herein incorporated by reference). Other embodiments are illustrated herein. See, FIG. 20.

An LNA monomer can refer to a conformationally restricted nucleotide analogue with an extra 2'-O, 4'-C-methylene bridge added to the ribose ring that may exhibit enhanced hybridization affinity towards complementary DNA and RNA. Evaluations of the influence of LNA residues on hybridization thermodynamics, counterions and hydration of DNA-DNA and DNA-RNA heteroduplexes were performed using spectroscopic and calorimetric techniques. Thermodynamic analysis for duplex formation using UV and differential scanning calorimetry suggested that LNA-induced stabilization results from a large, favorable increase in the enthalpy of hybridization that compensates for the unfavorable entropy change. The heat capacity change ($\Delta C_p$) accompanying the duplex formation may obtained through differential scanning calorimetry (DSC). Furthermore, it was observed that relative to the formation of unmodified duplex, the formation of LNA-modified duplexes may be accompanied by a higher uptake of counterions and a lower uptake of water molecules. Kaur et al., "Thermodynamic, counterion and hydration effects for the incorporation of locked nucleic acid (LNA) nucleotides in duplex" *Nucleic Acids Symp Ser (Oxf)*. 52:425-426 (2008).

Ligation-based methods have been disclosed for identifying at least two target nucleotides in a mixed population sample, that is a sample that contains or potentially contains target nucleic acid sequences from more than one source. Typically, two ligation reaction compositions comprising locked nucleic acids are formed, ligation products generated, and the ligation products or their surrogates are analyzed to identify target nucleotides in the mixed population sample. In certain embodiments, the target nucleic acid sequences, the ligation products, or both are amplified. In certain embodiments, multiplex amplification and/or ligation reactions are performed. Karger et al., "Methods and kits for identifying target nucleotides in mixed populations" U.S. Pat. No. 7,427, 479 (herein incorporated by reference).

In one embodiment, the present invention contemplates a SNAPPLE probe comprising an LNA binding partner may have affinity for an RNA. For example, an RNA may comprise a messenger RNA (mRNA). In one embodiment, the mRNA binds a plurality of different SNAPPLE probes at different binding sites. Although it is not necessary to understand the mechanism of an invention, it is believed that two SNAPPLE probes may bind to different regions of an RNA molecule, demonstrating that these regions come into close proximity. See, FIG. 19.

In one embodiment, the present invention contemplates a SNAPPLE probe comprising an LNA binding partner may have affinity for a DNA. For example, a DNA may comprise a double stranded DNA, a single stranded DNA, or a cDNA. In one embodiment, the DNA binds a plurality of different SNAPPLE probes at different binding sites. Although it is not necessary to understand the mechanism of an invention, it is believed that two SNAPPLE probes may bind to different regions of an DNA molecule, demonstrating that these regions come into close proximity.

C. Intracellular Receptor Binding Partners

Two basic types of receptor transducing systems have been reported: i) those which utilize transmembrane receptors that may be activated, for example, at the cell surface by an appropriate hormone or biochemical, thereby releasing intracellular second messenger molecules (i.e. cAMP), and; ii) those that utilize internal, cytoplasmic or nuclear receptors (i.e., for example, intracellular receptors) which, upon activation, may interact directly with DNA to alter the genetic program of a cell, or facilitate other intracellular biochemical processes (i.e., for example, calcium regulation). McDonnell et al., "Nuclear hormone receptors as targets for new drug discovery" *Biotechnology* (NY) 11:1256-1261 (1993).

In one embodiment, the present invention contemplates a SNAPPLE probe comprising a binding partner, wherein the partner comprises an intracellular receptor molecule. In one embodiment, the receptor molecule may comprise a membrane bound receptor. In one embodiment, the receptor molecule may comprise a soluble receptor. In one embodiment, the intracellular receptor may have affinity for a binding ligand selected from the group comprising a peptide, a hormone, a neurotransmitter, or cofactors.

In one embodiment, the present invention contemplates a method providing at least two SNAPPLE probes, wherein each probe comprises affinity for a different binding ligand for detecting the spatial proximity between at least two different intracellular receptor molecules.

In one embodiment, the present invention contemplates a method providing at least two SNAPPLE probes, wherein each probe comprises a receptor subunit as a binding partner. In one embodiment, the first probe comprises a first receptor subunit. In one embodiment, the second probe comprises a second receptor subunit. In one embodiment, the second binding ligand comprises an affinity for a cofactor subunit. Although it is not necessary to understand the mechanism of an invention, it is believed that binding the probes to a receptor may determine conformation changes in a receptor molecule upon interaction with a binding ligand.

1. Calcium Regulation

It is believed that an intracellular receptor specific for cyclic ADP-ribose (cADPR) exists and is different from the inositol trisphosphate (IP3) receptor. cADPR is a metabolite of $NAD^+$ which is as active as IP3 in mobilizing intracellular $Ca^{2+}$ in sea urchin eggs. The enzyme responsible for synthesizing cADPR is found not only in sea urchin eggs but also in various mammalian tissue extracts, suggesting that it may be a general messenger for $Ca^{2+}$ mobilization in cells. Sea urchin eggs were homogenized and the $Ca^{2+}$-storing microsomes were separated from mitochondria and other organelles by Percoll density centrifugation. Radioactive cADPR with high specific activity was produced by incubating $[^{32}P]NAD^+$ with the synthesizing enzyme and the product purified by high pressure liquid chromatography. The enzyme was membrane bound and was isolated from dog brain extracts by sucrose density gradient centrifugation. Partial purification of the enzyme was achieved by DEAE ion-exchange chromatography after solubilization with 3-[(cholamidopropyl) dimethylammonio]-1-propanesulfonate. Specific binding of $^{32}P$-labeled cADPR to a saturable site on the $Ca^{2+}$-storing microsomes was detected by a filtration assay. Scatchard analysis indicated a binding affinity of about 17 nM and a capacity of about 25 fmol/mg protein. The binding was not affected by either $NAD^+$ (the precursor) or ADP-ribose (the hydrolysis product) at 0.5 µM but was eliminated by 0.3 µM nonlabeled cADPR. The receptor for cADPR appeared to be different from that of IP3 since IP3 was not an effective competitor at a concentration as high as 3 µM. Similarly, heparin at a concentration that inhibits most of the IP3-induced calcium release from the microsomes did not affect the binding. The binding showed a prominent pH optimum at about 6.7. Calcium at 40 µM decreased the binding by about 50%. These dependencies of the binding on pH and $Ca^{2+}$ are different from those reported for the IP3 receptor and provide further support that the intracellular receptors for cADPR and IP3 are different. Lee H C., "Specific binding of cyclic ADP-ribose to calcium-storing microsomes from sea urchin eggs" *J Biol Chem.* 266:2276-2281 (1991).

$Ca^{2+}$ mobilization is believed mediated by intracellular receptors having affinity for inositol 1,4,5-trisphosphate (IP3). IP3 is believed to be a second messenger generated via receptor-stimulated hydrolysis of phosphatidylinositol 4,5-bisphosphate. Various reports suggest IP3 intracellular receptor localization at various subcellular structures including, but not limited to: i) elements of the endoplasmic reticulum (both rough and smooth surfaced regions); ii) the nuclear envelope, and iii) the plasma membrane. Immunofluorescent polyclonal monospecific antibodies directed against the inositol 1,4,5-trisphosphate receptor in central nervous system tissue detected receptors localized in Purkinje cells, whereas the cerebellar cortex remained negative. The visualized IP3 receptors were concentrated in cisternal stacks (piles of up to 12 parallel cisternae separated by regularly spaced bridges, located both in the deep cytoplasm and beneath the plasma membrane; average density, greater than 5 particles/micron of membrane profile); in cisternal singlets and doublets adjacent to the plasma membrane (average density, approximately 2.5 particles/micron); and in other apparently smooth-surfaced vesicular and tubular profiles. In the dendrites, approximately half of the nonmitochondrial, membrane-bound structures (cisternae, tubules, and vesicles), as well as small cisternal stacks, were labeled. Dendritic spines always contained immunolabeled cisternae and vesicles. These results identify a large, smooth-surfaced endoplasmic reticular subcompartment that appears to play a role in the control of $Ca^{2+}$ homeostasis. Satoh et al., "The inositol 1,4,5,-trisphosphate receptor in cerebellar Purkinje cells: quantitative immunogold labeling reveals concentration in an ER subcompartment" *J Cell Biol.* 111:615-624 (1990).

The visinin-like protein (VSNL) subfamily, including VILIP-1 (the founder protein), VILIP-2, VILIP-3, hippocalcin, and neurocalcin delta, constitute a highly homologous subfamily of intracellular neuronal calcium sensor (NCS) proteins. These proteins display differences in their calcium affinities, in their membrane-binding kinetics, and in the intracellular targets to which they associate after calcium binding. Even though the proteins use a similar calcium-myristoyl switch mechanism to translocate to cellular membranes, they show calcium-dependent localization to various subcellular compartments when expressed in the same neuron. These distinct calcium-myristoyl switch properties might be explained by specificity for defined phospholipids and membrane-bound targets; this enables VSNLs to modulate various cellular signal transduction pathways, including cyclic nucleotide and MAPK signaling. VSNLs may directly or indirectly effect gene expression and/or interact with components of membrane trafficking complexes, thereby having a possible role in membrane trafficking of different receptors and ion channels, including, but not limited to, glutamate receptors of the kainate and AMPA subtype, nicotinic acetylcholine receptors, and $Ca^{2+}$-channels. Braunewell et al., "Visinin-like proteins (VSNLs): interaction partners and emerging functions in signal transduction of a subfamily of neuronal $Ca^{2+}$-sensor proteins" *Cell Tissue Res.* 335(2):301-316 (2009).

2. Eicosanoids

Eicosanoids are produced by many different cell types through their ligation and activation of specific membrane-bound and intracellular receptors. They are believed to regulate a myriad of physiological and pathological functions, including, for example, body temperature. While the thermoregulatory role of eicosanoids has mainly been associated with illness-induced fever, they are unlikely to be involved in the maintenance of normal body temperature. Aronoff et al., "Eicosanoids in non-febrile thermoregulation" *Prog Brain Res* 162:15-25 (2007).

3. Protein Kinase C

Protein kinase C (PKC) translocates from the soluble to the cell particulate fraction on activation. Intracellular receptors that bind activated PKC in the particulate fraction have been implicated by a number of studies. Previous work identified 30- to 36-kDa proteins in the particulate fraction of heart and brain that bound activated PKC in a specific and saturable manner. These proteins were termed intracellular Receptors for Activated C-Kinase, or RACKs. Cloning of a cDNA encodes a 36-kDa protein (RACK1) that comprises RACK functionality. for example: (i) RACK1 bound PKC in the presence of PKC activators, but not in their absence; (ii) PKC binding to the recombinant RACK1 was not inhibited by a pseudosubstrate peptide or by a substrate peptide derived from the pseudosubstrate sequence, indicating that the binding did not reflect simply PKC association with its substrate; (iii) binding of PKC to RACK1 was saturable and specific; two other protein kinases did not bind to RACK1; (iv) RACK1 contains two short sequences homologous to a PKC binding sequence previously identified in annexin I and in the brain PKC inhibitor KCIP. Further, peptides derived from these sequences inhibited PKC binding to RACK1. In vitro data also suggest a role for RACK1 in PKC-mediated signaling. Ron et al., "Cloning of an intracellular receptor for protein kinase C: a homolog of the beta subunit of G proteins"

*Proc Natl Acad Sci USA.* 91:839-843 (1994). RACK1 is a homolog of the beta subunit of G proteins, which were recently implicated in membrane anchorage of the beta-adrenergic receptor kinase. Pitcher et al., *Science* 257:1264-1267 (1992).

Isoforms of the phospholipid-dependent protein kinase, protein kinase C (PKC), may also be intracellular receptors for diacylglycerol. Cytoplasmic nPKCΔ and nPKCε have been reported to detect increases in membrane diacylglycerols and translocate to the membrane. This brings about PKC activation, though modifications additional to binding to phospholipids and diacylglycerol are involved. The next event (probably associated with PKC activation) is the activation of the membrane-bound small G protein Ras by exchange of GTP for GDP. RasGTP loading translocates Raf family mitogen-activated protein kinase (MAPK) kinase kinases to the membrane, initiates the activation of Raf, and thus activates the extracellular signal-regulated kinase ½ (ERK½) cascade. Over longer times, two analogous protein kinase cascades, the c-Jun N-terminal kinase and p38-mitogen-activated protein kinase cascades, become activated. As the signals originating from the ET(A) receptor are transmitted through these protein kinase pathways, other signaling molecules become phosphorylated, thus changing their biological activities. For example, ET-1 increases the expression of the c-jun transcription factor gene, and increases abundance and phosphorylation of c-Jun protein. These changes in c-Jun expression and phosphorylation are likely to be important in the regulation of gene transcription. Sugden et al., "Endothelin signalling in the cardiac myocyte and its pathophysiological relevance" *Curr Vase Pharmacol.* 3:343-351 (2005).

4. Steroids

Interactions between polymers and intracellular estrogen receptors were studied in the context of tumoral indicators of breast cancer. These polymers were used as microcarriers for MCF7 cell cultures, a cellular model of human breast cancer. Quantification of MCF7 cell estrogen receptors was determined by radioligand binding assay for different days of cellular proliferation. These polymers demonstrated an inverse relationship between inhibition of cell proliferation and increased intracellular estrogen receptors. Mestries et al., "Interactions between biospecific polymers and MCF7 cells: modulation of cellular proliferation and expression of estrogen receptors" *Bull Cancer.* 84:1017-1023 (1997)

In the past, the intracellular response of target cells to the steroid hormone aldosterone has been divided into acute non-genomic (<10 min) and sustained genomic (>10 min) action. Atomic force microscopy (AFM) observations in living endothelial cells demonstrate that aldosterone induces cell volume increase in less than 10 minutes, thereby identifying the cell nucleus as the swelling site. Hormone-induced nuclear swelling can reach 15 to 28% of total cell volume dissipating within 30 minutes. AFM-investigation of the intracellular signal pathway in nuclear envelope of aldosterone-injected Xenopus laevis oocytes visualizes putative intracellular receptors (40 kD granules) bound to nuclear pores 2 minutes after hormone injection, with subsequent macromolecule translocation into the nucleus. 15 minutes later macromolecules (800 kD plugs) appear in the central channels of the nuclear pores. The plugs resemble ribonucleoproteins that carry the aldosterone-induced mRNA to the ribosomes. It is believed that steroid-induced nuclear swelling is caused by a shift of receptors/transcription factors from cytoplasm into nucleoplasm followed by gene transcription. Nuclear volume returns to normal when mRNA export through the nuclear pores is finished. Thus, steroid-induced net-movements of macromolecules between intracellular compartments initiate shifts in cell volume compensated by volume regulatory transporters and ion channels in the plasma membrane. Oberleithner et al., "Aldosterone and nuclear volume cycling" *Cell Physiol Biochem* 10:429-434 (2000).

It is believed that intracellular corticosteroid receptors may mediate tissue effects of glucocorticoids in vertebrates including, but not limited to, two intracellular receptors that act primarily as ligand-activated transcription factors and a membrane-associated receptor. Some intracellular steroid receptor subtypes have been well characterized in mammals. Breuner et al., "Pharmacological characterization of intracellular, membrane, and plasma binding sites for corticosterone in house sparrows" *Gen Comp Endocrinol.* (Epub. Feb. 21, 2009)

Many of the biological actions of progestins may depend on binding to intracellular receptors and through a long chain of events to subsequent stimulation of transcriptional activity and protein synthesis. This process requires at least a few hours in time and many different coregulator proteins play a role after progestin binding to its receptor. Thijssen J H., "Gene polymorphisms that may influence the biological effects of progestins" *Maturitas* (Epub Jan. 6, 2009).

5. Apoptosis

Ribonucleic acid interference (RNAi)-mediated knockdown of the intracellular receptors NALP3 or MDA5 did not affect poly(I:C)-induced pro-IL-1beta mediated apoptosis. Stimulation of membrane-bound Toll-like receptors (TLRs) may up-regulate pro-IL-1β expression, activate caspase-1, and is believed to be mainly initiated by cytosolic Nod-like receptors. Polyinosinic:polycytidylic acid (poly[I:C]) and lipopolysaccharide stimulation of macrophages may induce pro-IL-1β processing via a Toll/IL-1R domain-containing adaptor-inducing interferon-beta-dependent signaling pathway that is initiated by TLR3 and TLR4, respectively. Consequently, caspase-8 may play a role in the production of biologically active IL-1β in response to TLR3 and TLR4 stimulation. Maelfait et al., "Stimulation of Toll-like receptor 3 and 4 induces interleukin-1β maturation by caspase-8" *J Exp Med.* 205:1967-1973 (2008).

Toxic agents, particularly those that exert their actions with a great deal of specificity, sometimes act via intracellular receptors to which they bind with high affinity. Some examples include, but are not limited to, soluble intracellular receptors, which may be important in mediating toxic responses. For example, an intracellular glucocorticoid receptor may mediate toxicity associated effects such as apoptosis of lymphocytes as well as neuronal degeneration as a response to stress. The peroxisome proliferator activated receptor (PPAR) may be associated with hepatocarcinogenesis in rodents. The dioxin receptor may mediate a more generalized response to toxin exposure. Gustafsson J A., "Receptor-mediated toxicity" *Toxicol Lett.* 82-83:465-470 (1995)

6. Hormone Regulation

In HEK 293 and COS7 cells, thyrotropin-releasing hormone (TRH) receptors are believed to be predominantly intracellular. In transiently transfected COS7 cells, the TRH receptor colocalized with endoplasmic reticulum and Golgi markers. The pattern of TRH receptor immunofluorescence was the same over a wide range of receptor expression in transiently transfected COS7 cells, and all cell lines bound similar amounts of $^3$H- and rhodamine-labeled TRH analogs, suggesting that cell-specific differences in TRH receptor localization were not simply the result of overexpression. In all cell contexts, TRH receptors on the plasma membrane underwent extensive ligand-driven endocytosis. Inhibitors of glycosylation did not alter the subcellular distribution of receptors. In HEK 293 cells expressing the transfected TRH receptor, protein synthesis inhibitors caused translocation of intracellular receptors to the cell surface, as shown by a marked increase in cell surface immunofluorescence and [$^3$H][N3-methyl-His2]TRH binding. The localization of an epitope-tagged receptor for TRH expressed in different cell contexts was studied with immunofluorescence microscopy. In pituitary lactotrophs, which normally express TRH receptors, and in AtT20 pituitary corticotrophs, TRH receptor immunoreactivity was primarily confined to the plasma membrane. These results demonstrate that the subcellular localization of the TRH receptor depends on the cell context in which it is expressed and that intracellular receptors are capable of translocation to the plasma membrane. Yu et al., "Effect of cell type on the subcellular localization of the thyrotropin-releasing hormone receptor" *Mol Pharmacol.* 51:785-793 (1997).

7. Nitric Oxide

It has been suggested that, in physiological conditions, myoglobin acts as intracellular scavenger preventing nitric oxide (NO) from reaching its intracellular receptors in cardiomyocytes. In myoglobin-deficient conditions, NO is able to reduce contractility via activation of the soluble guanylyl cyclase/cyclic GMP pathway. NO donors may include, but are not limited to, S-nitroso-N-acetylpenicillamine (SNAP), sodium(Z)-1-(N,N-diethylamino) diazen-1-ium-1,2-diolate (DEA-NONOate), and (Z)-1-[N-(2-Aminoethyl)-N-(2-ammonio ethyl)amino]diazen-1-ium-1,2-diolate (DETA-NONOate). Specifically, SNAP slightly reduced contractility in preparations from wild type mice at concentrations above 100 μM and was more pronounced in myo$^{-/-}$ mice. DEA-NONOate and DETA-NONOate also reduced contractility in preparations from myo$^{-/-}$ mice more than wild type mice. Pre-incubation with an inhibitor of the soluble guanylyl cyclase (i.e., for example, 1H-[1,2,4]oxadiazolo[4,3-a]quinoxalin-1-one; 100 μM) prevented the effects of the NO donors on contractility in myo$^{-/-}$ mice. Wegener et al., "Effects of nitric oxide donors on cardiac contractility in wild-type and myoglobin-deficient mice" *Br J Pharmacol.* 136:415-420 (2002).

D. Biological Cell Binding Partners

In one embodiment, the present invention contemplates a SNAPPLE probe comprsing a binding partner, wherein the partner comprising a biological cell. In one embodiment, the cell comprising a blood cell. In one embodiment, the blood cell comprises a white blood cell. In one embodiment, the white blood cell comprises a lymphocyte. In one embodiment, the cell comprises and antigen presenting cell. In one embodiment, the cell comprises a stem cell. In one embodiment, the stem cell comprises a bone marrow cell. In one embodiment, the stem cell comprises an embryonic stem cell. In one embodiment, the stem cell comprises an epithelial stem cell. In one embodiment, the stem cell comprises an endothelial stem cell. In one embodiment, the endothelial stem cell comprises a cardiovascular endothelial stem cell.

E. Derivatized Bead Binding Partners

In one embodiment, the present invention contemplates a SNAPPLE probe comprsing a binding partner, wherein the partner comprising a derivatized bead. In one embodiment, the bead comprises an Fab fragment. In one embodiment, the bead comprises an LNA sequence. In one embodiment, the bead comprises a DNA sequence. In one embodiment, the bead comprises a small organic molecule. In one embodiment, the small organic molecule comprises a drug.

A preferred embodiment includes polystyrene beads, between 10-100 microns in diameter, which are capable of substantially homogeneous dispersion and separation from a medium by filtration or floatation. Another preferred embodiment includes ferromagnetic beads. A ferromagnetic bead marketed under the trademarks BIO-MAG is capable of substantially homogeneous dispersion in an aqueous medium and can be retrieved or immobilized by an electromagnetic field. The ferromagnetic bead includes an iron core which is coated with an amine reactive covering. The beads are generally spherical and have a diameter of one micron. The polystyrene and ferromagnetic beads are treated to include antiligand moieties.

Beads (i.e., for example, a polystyrene bead) having reactive amine functional groups can be reacted with polynucleotides to covalently affix the polynucleotide to the bead. The beads are reacted with 10 percent glutaraldehyde in sodium phosphate buffer and subsequently reacted in a phosphate buffer with ethylene-diamine adduct of the phosphorylated polynucleotide.

One method of covalently binding a binding partner to derivatize a bead comprises a chemical conjugation agent to activate the bead, followed by the attachment of the binding partner to the conjugation agent. Synthetic polymeric beads are advantageous because they can withstand harsh derivatization conditions and are relatively inexpensive, and often yield a linkage that is stable to a wide range of denaturing conditions. A number of derivatized beads are commercially available, all with various constituents and sizes. Beads formed from synthetic polymers include, but are not limited to, polyacrylamide, polyacrylate, polystyrene, or latex are commercially available from numerous sources such as Bio-Rad Laboratories (Richmond, Calif.) and LKB Produkter (Stockholm, Sweden). Beads formed from natural macromolecules and particles include, but are not limited to, agarose, crosslinked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia. Magnetic beads are commercially available from sources such as Dynal Inc. (Great Neck, N.Y.).

F. Small Organic Molecule Binding Partners

In one embodiment, the present invention contemplates a SNAPPLE probe comprising a binding partner, wherein the partner comprises a small organic molecule. In one embodiment, the small organic molecule may comprise a second messenger. In one embodiment, the small organic molecule may comprise an enzymatic cofactor. In one embodiment, the second messenger may include, but not limited to, cyclic AMP, cyclic GMP, prostaglandins, diacylglycerols, or an inositol phosphate.

III. Asymmetric Barcode Amplification

In one embodiment, the present invention contemplates a composition comprising an asymmetric nucleotide barcode sequence. In one embodiment, the present invention contemplates a method comprising amplifying an asymmetric nucleotide barcode thereby creating a plurality of amplicons. In one embodiment, the amplicon comprises the nucleic acid sequence of the asymmetric nucleotide barcode. In one embodiment, the method further comprises identifying the amplicon nucleic acid sequence by a sequencing technique. In one embodiment, the method further comprises comparing the amplicon nucleic acid sequence to a SNAPPLE probe unique nucleotide barcode. In one embodiment, the method further comprises identifying an intracellular component associated with the SNAPPLE probe unique nucleotide barcode.

Polymerase chain reaction (PCR) technology amplifies a specific DNA segment when flanked by a set of primers. R. K. Saiki et al., Science 230, 1350 (1985); Erlich, D. Gelfand, J. J. Sninsky, Science 252, 1643 (1991). The PCR process thereby allows the production of large amounts of specific DNA products (i.e., for example, amplicons), which can be detected by various methods (i.e., for example, gel electrophoresis isolation and sequencing). The selected primer pair is believed responsible for the high specificity of PCR for a target sequence. PCR was initially used to detect antigen-antibody complexes in a protocol termed, Immuno-PCR. In Immuno-PCR, a linker molecule with bispecific binding affinity for DNA and antibodies is used to attach a DNA molecule (marker) specifically to an antigen-antibody complex, resulting in the formation of a specific antigen-antibody-DNA conjugate. The present invention improves upon the basic tenets of Immuno-PCR such that more than one target antigen can be identified, in addition to providing spatial proximity information.

IV. Intracellular Component Contact Maps

In one embodiment, the present invention contemplates a method, providing a plurality of SNAPPLE probes and introducing the probes into a cell, wherein the cell comprises a plurality of intracellular components. In one embodiment, at least one probe comprises a binding partner having affinity for a first intracellular component. In one embodiment, the intracellular component comprises a protein. In one embodiment, the intracellular component comprises an intracellular receptor. In one embodiment, the intracellular component comprises a small organic molecule. In one embodiment, the cell comprises a cell cycle phase. In one embodiment, the cell is exposed to a specific temperature. In one embodiment, the cell is exposed to a drug. In one embodiment, the cell is exposed to a toxin. In one embodiment, the cell is exposed to radiation. In one embodiment, the method further comprises binding the binding partner to the intracellular component under conditions such that the probe pairs create an asymmetric nucleotide barcode. In one embodiment, the method further comprises identifying the asymmetric nucleotide barcodes, thereby creating an intracellular component contact map. In one embodiment, the contact map comprises a heat map.

Color mapping of intracellular component paring data using contour color mapping approaches may be found in two, three, and four dimensional contour heatmaps. Contour color heatmapping uses the entire data space or data matrix (image) as the basis for the color process. Color intensity may thereby reflect that amount of data being processed for any particular data point (i.e, is proportional to the frequency of isolated asymmetric nucleotide barcode sequences).

In one embodiment, the present invention contemplates a heatmap comprising an array comprising rows and columns. In one embodiment, the rows comprise UNB's intracellular compnents A-Z. In one embodiment, the columns comprise DNB's for intracellular components A-Z. In one embodiment, an array comprising a color intensity at a specific row-column intersection indicates that the row intracellular component and the column intracellular component interact (i.e., were present in close proximity). In one embodiment, the color intensity is proportional to the observed frequency of the intracellular component interaction.

Systems biology aims to understand biological systems on a comprehensive scale, such that the components that make up the whole are connected to one another and work through dependent interactions. Molecular correlations and comparative studies of molecular expression can establish interdependent connections in systems biology. Commercially available software packages provide limited data mining capability. These programs require the user to first generate visualization data with a preferred data mining algorithm and then upload the resulting data into the visualization package for graphic visualization of molecular relations. Alternative interactive visual data mining applications, (i.e., for example, SysNet) provide an interactive environment for the analysis of high data volume molecular expression information of most any type from biological systems. The interactive nature of the program presents intermolecular correlation information compatible with heatmap layouts. Zhang et al., "Interactive analysis of systems biology molecular expression data" *BMC Syst Biol.* 2:23 (2008).

Large quantities of chemical structure and biological activity data brought about through combinatorial chemistry and high-throughput screening technologies has created the need for sophisticated graphical tools to evaluate the data. Many chemoinformatics software applications apply standard clustering techniques to organize structure-activity data, but they differ significantly in their approaches to visualizing clustered data. For example, Molecular Property eXplorer (MPX) can presents clustered data in the form of heatmaps. MPX employs agglomerative hierarchical clustering to organize data on the basis of the similarity between 2D chemical structures or similarity across a predefined profile of biological assay values. Visualization of hierarchical clusters as heatmaps provides simultaneous representation of cluster members along with their associated assay values. Heatmaps provide visualization of the cluster members across an activity profile. Kibbey et al., "Molecular Property eXplorer: a novel approach to visualizing SAR using tree-maps and heatmaps" *J Chem Inf Model.* 45:523-32 (2005).

A. Cell Cycles

The cell cycle, or cell-division cycle, is the series of events that take place in a cell leading to its division and duplication (replication). In cells without a nucleus (prokaryotes), the cell cycle occurs via a process termed binary fission. In cells with a nucleus (eukaryotes), the cell cycle can be divided in two brief periods: interphase—during which the cell grows, accumulating nutrients needed for mitosis and duplicating its DNA—and the mitotis (M) phase, during which the cell splits itself into two distinct cells, often called "daughter cells". The cell-division cycle is a vital process by which a single-celled fertilized egg develops into a mature organism, as well as the process by which hair, skin, blood cells, and some internal organs are renewed. The cell cycle consists of four distinct phases: $G_1$ phase, S phase (synthesis), $G_2$ phase (collectively known as interphase) and M phase (mitosis). M phase is itself composed of two tightly coupled processes: mitosis, in which the cell's chromosomes are divided between the two daughter cells, and cytokinesis, in which the cell's cytoplasm divides forming distinct cells. Activation of each phase is dependent on the proper progression and completion of the previous one. Cells that have temporarily or reversibly stopped dividing are said to have entered a state of quiescence called $G_0$ phase.

Prokaryotic cell cycles have been studied using bacterial models. Despite their small size and lack of obvious intracellular structures, bacteria have a complex and dynamic intracellular organization. Recent work has shown that many proteins, and even regions of the chromosome, are localized to specific subcellular regions that can change over time, sometimes extraordinarily fast. Protein function can depend on cellular position, so the analysis of the intracellular location of a protein can be crucial for understanding its activity.

Because regulatory proteins are among those that reside at specific cellular sites, it is now necessary to consider three-dimensional organization when describing the genetic networks that control bacterial cells. Jensen et al., "Proteins on the move: dynamic protein localization in prokaryotes" *Trends Cell Biol.* 10:483-488 (2000).

Bacteria exhibit a high degree of intracellular organization, both in the timing of essential processes and in the placement of the chromosome, the division site, and individual structural and regulatory proteins. Mechanisms that control timing of cell cycle and developmental events include transcriptional cascades, regulated phosphorylation and proteolysis of signal transduction proteins, transient genetic asymmetry, and intercellular communication. Surprisingly, many signal transduction proteins are dynamically localized to specific subcellular addresses during the cell division cycle and sporulation, and proper localization is essential for their function. For example, the Min proteins that govern division site selection in *Escherichia coli* may be the first example of a system that generates positional information de novo. Ryan et al., "Temporal and spatial regulation in prokaryotic cell cycle progression and development" *Annu Rev Biochem.* 72:367-394 (2003).

The small nuclear GTPase Ran is believed to control the directionality of macromolecular transport between the bacterial nucleus and the cytoplasm. Ran also may have a role during mitosis, when the nucleus is reorganized to allow chromosome segregation. Therefore, Ran may direct the assembly of the mitotic spindle, nuclear-envelope dynamics and the timing of cell-cycle transitions. Such functions reflect the spatial and temporal coordination of the changes that occur in intracellular organization during the cell-division cycle. Clarke et al., "Spatial and temporal coordination of mitosis by Ran GTPase" *Nat Rev Mol Cell Biol.* 9:464-477 (2008).

A-kinase-anchoring proteins (AKAP) may help regulate the intracellular organization of cyclic AMP-dependent kinase (PKA) and actin within somatic cells. Elevated levels of cAMP also help maintain meiotic arrest in immature oocytes, with AKAPs implicated as potential mediators. Studies have suggested that WAVE1 sequestration to the nucleus may occur during fertilization, and is an actin-independent event that relies on dynamic microtubules but not nuclear pores. Rawe et al., "WAVE1 intranuclear trafficking is essential for genomic and cytoskeletal dynamics during fertilization: cell-cycle-dependent shuttling between M-phase and interphase nuclei." *Dev Biol.* 276:253-267 (2004)

The high mobility group N (HMGN) proteins are a family of nuclear proteins that bind to nucleosomes, changes the architecture of chromatin, and enhances transcription and replication from chromatin templates. The intracellular organization of the HMGN (previously known as HMG-14/17) proteins is dynamic and is related to both cell-cycle and transcriptional events. These proteins roam the nucleus, perhaps as part of multiprotein complexes, and their target interactions are modulated by posttranslational modifications. Functional studies on HMGN proteins provide insights into the molecular mechanisms by which structural proteins affect DNA-dependent activities in the context of chromatin. Bustin M., "Chromatin unfolding and activation by HMGN chromosomal proteins" *Trends Biochem Sci.* 26:431-437 (2001)

B. Temperature

It has been previously demonstrated that plant cells (i.e., for example, Nicotiana plumbaginifolia) react to cold-shock by an immediate rise in cytosolic calcium. Cytoskeleton organization has also been shown to have profound influences on the temperature-induced calcium response. For example, the disruption of the microtubule meshwork by various active drugs, such as colchicin, oryzalin and vinblastin, leads to increases in the cytosolic calcium (up to 400 nM) in cold-shocked protoplasts over control. The cytoskeleton may play a role in controlling the intensity of calcium responses to an extracellular stimulus (i.e., for example, temperature fluctuations). Mazars et al., "Organization of cytoskeleton controls the changes in cytosolic calcium of cold-shocked Nicotiana plumbaginifolia protoplasts" *Cell Calcium* 22:413-20 (1997).

C. Drugs And Toxins

The transition of adult rat aortic smooth muscle cells from a contractile to a synthetic phenotype during the first week of primary culture on a substrate of fibronectin in serum-free medium was studied by light and electron microscopy. The weak base chloroquine and the carboxylic ionophore monensin were both found to inhibit the spreading of the cells and the accompanying changes in cellular fine structure. The exchange of myofilament bundles for a prominent rough endoplasmic reticulum and Golgi complex was delayed and vacuoles filled with incompletely degraded material accumulated in the cytoplasm. The microtubule-disruptive drugs colchicine and nocodazole likewise opposed the spreading and fine structural reorganization of the cells. Most typically, the Golgi stacks were small and widely dispersed. In addition, vacuoles of the type mentioned above increased in number. On the other hand, there was surprisingly little effect of cytochalasin B, a drug that is supposed to interfere with the assembly of actin filaments. The observations suggest that the phenotypic modulation of arterial smooth muscle cells is dependent on: (a) lysosomal degradation of discarded cellular constituents, (b) active vesicular transport along the exocytic pathway to provide the expanding cell surface with new membrane, and (c) a normal microtubular cytoskeleton to ensure the establishment of a new and functionally efficient intracellular organization. Thyberg et al., "Phenotype modulation in primary cultures of rat aortic smooth muscle cells. Effects of drugs that interfere with the functions of the vacuolar system and the cytoskeleton" *Virchows Arch B Cell Pathol Incl Mol Pathol.* 59:1-10 (1990)

V. Antibodies

The present invention provides isolated antibodies (i.e., for example, polyclonal or monoclonal). In one embodiment, the present invention provides monoclonal antibodies that specifically bind to an intracellular component including, but not limited to, a protein, a glycoprotein, a lipid, a glycolipid, or a nucleic acid.

For example, an antibody against a protein may be any monoclonal or polyclonal antibody, as long as it can recognize the protein. Antibodies can be produced by using a protein of the present invention as the antigen according to a conventional antibody or antiserum preparation process. Any suitable method may be used to generate the antibodies used in the methods and compositions of the present invention. For example, a monoclonal antibody may be prepared by administering a protein, optionally with a suitable carrier or diluent, to an animal (e.g., a mammal) under conditions that permit the production of antibodies (i.e., for example, immunization). For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal (e.g., a mouse) whose antibody titer has been confirmed is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% CO2 gas. The antibody titer of the supernatant of a hybridoma culture can be measured according to the same manner as described above with respect to the antibody titer of the anti-protein in the antiserum. Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from an animal or human. For example, a complex of an immunogen (an antigen against the protein) and a carrier protein is prepared and an animal or human is immunized by the complex according to the same manner as that described with respect to the above monoclonal antibody preparation. A material containing the antibody against is recovered from the immunized animal or human and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten. In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times. The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

VI. Detection Methodologies

A. Detection of RNA mRNA expression may be measured by any suitable method, including but not limited to, those disclosed below.

In some embodiments, RNA is detection by Northern blot analysis. Northern blot analysis involves the separation of RNA and hybridization of a complementary labeled probe. In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes. In still further embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLI-TAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Detection of Protein

In other embodiments, protein may be detected by any suitable method. In some embodiments, proteins are detected by immunohistochemistry. In other embodiments, proteins are detected by their binding to an antibody raised against the protein.

Antibody binding may be detected by many different techniques including, but not limited to, (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, and immuno-electrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

C. Remote Detection Systems

In some embodiments, a computer-based analysis program is used to translate the raw data generated by the detection assay (e.g., the presence, absence, or amount of a given marker or markers) into data useful for intracellular component contact mapping.

The present invention contemplates any method capable of receiving, processing, and transmitting the information to and from laboratories conducting the assays, wherein the information is provided to appropriate personnel. For example, in some embodiments of the present invention, a sample (e.g., a biopsy or a serum or urine sample) is obtained from a subject and submitted to an intracellular component profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

D. Detection Kits

In other embodiments, the present invention provides kits for the detection and characterization of intracellular contact maps. In some embodiments, the kits contain antibodies specific for protein pairs in addition to detection reagents (i.e., for example, SNAPPLE probes) and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

VII. Kits

In another embodiment, the present invention contemplates kits for the practice of the methods of this invention. The kits preferably include one or more containers containing elements according the described methods of this invention. The kit can optionally include a first container comprising a plurality binding partners, wherein each partner is attached to a different forked adapter molecule. The kit can optionally include a second container comprising a solution capable of fixing a biological cell sample. The kit can optionally include a third container comprising buffers and reagents capable of supporting binding of said binding partner to intracellular components of said fixed biological cell sample. The kit can optionally include enzymes capable of performing PCR (i.e., for example, DNA polymerase, Tag polymerase and/or restriction enzymes). The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle. The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in how to identify said intracellular components bound to said binding partners. In particular, the instructions may describe construction of an intracellular component contact map. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

Example I

Conjugation of Antibodies to Nucleotides

Antibodies may be coupled to oligonucleotides using aldehyde/hydrazine chemistry (Solulink inc.), and purified by size exclusion chromatography, and then stored at +4° C. in PBSE with sodium azide. Kozlov, I. A. "Efficient strategies for the conjugation of oligonucleotides to antibodies enabling highly sensitive protein detection" Biopolymers 73:621-30 (2004). In general, affinity purified polyclonal antibodies and antigen standards may be obtained from R&D systems and BD Biosciences. Sequences may be designed to minimize probe-probe heteroduplexes using mFold[2]. A 1 mg batch of a polyclonal proximity probe may be sufficient for over 10 million analyses and the reagents are stable in storage.

Specifically, a pure antibody may be used without carrier proteins as BSA or gelatin. Dialyze the antibodies against PBS if they contain azide. Concentrate by spin columns (Microcon YM-30, Amicon Cat no 42410), if needed, to a concentration higher than 2 mg/ml.

1. Exchange buffer in the antibody to 55 mM Phosphate buffer, 150 mM NaCl, 20 mM EDTA, pH 7.2.
2. To 20 µg Antibody (10 µl) add 1 µl 4 mM sulfo-SMCC (diluted in DMSO) and incubate at room temp for 2 hrs.
3. Reduce 3 µl of 100 µM Oligo with 4 µl of 100 mM DTT in 50 µl of 55 mM Phosphate buffer, 150 mM NaCl 20 mM EDTA pH 7.2 for 1 hr at 37° C.
4. Equilibrate G-50 spin columns (Amersham Cat no 27-5330-02) with 55 mM Phosphate buffer, 150 mM NaCl, 20 mM EDTA, pH 7.2
5. Do buffer exchange of both the sulfo-SMCC activated antibodies and reduced oligos with the G-50 columns from above. Repeat twice per sample.
6. Mix the antibodies and oligos and dialyze (Slide-A-Lyzer, Pierce Cat no 69562) against PBS, 5 mM EDTA pH 7.2 over night.
7. Collect the dialyzed conjugates and store them at +4° C.

Example II

Plasma Samples

EDTA plasma samples may be collected and fresh frozen in aliquots at −80° C. Prior to analysis, PEG-8000 may be added to a final concentration of 5% and incubated at +4° C. for 30 min then centrifuged at 4,000 rpm for 20 minutes to remove potential assay interferences.

Example III

Probe-Target Binding Incubation

One µL of each sample may be added to 1 µL of a probe mix resulting in a 100 pM concentration of each probe in PBS pH 7.2, 20 µg/mL sheared poly-A (Sigma), 2 mM EDTA, 1% BSA, 0.05% bulk goat IgG. Incubations were performed at 37° C. for 2 hours.

Example IV

Ligation

120 µL ligation mixes may be added containing 100 nM connecting oligonucleotides, 2.5 units of Ampligase (Epicentre), 0.3 mM NADH$^+$ (Sigma), 10 mM DTT, 20 mM Tris-HCl pH 8.3, 50 mM KCl, 1.5 mM MgCl$_2$. Ligation proceeded at 30° C. for 15 minutes. Ligation was terminated by adding 0.25 µL of the uracil excision mix (Epicentre) degrading the uracil containing connectors.

Example V

Amplification of a Barcoded Amplicon Pool

25 µL of the ligation reaction may be amplified in a 50-µL PCR using 200 nM universal primers amplifying all sequences for 13 cycles. The product may then be diluted 50-fold in 1×TE-buffer prior to real-time PCR.

Example VI

Real-Time PCR

2 µLs of the diluted pre-amplification reaction may be added to the qPCR mixture to a volume of 10 µL containing iTaq qPCR Sybr Green master mix with ROX (Bio-Rad) with 0.4 µM of respective target specific primer. Samples were run on a 384 well ABI 7900 with the default cycling protocol.

We claim:

1. A composition comprising a forked adapter molecule comprising a first end and a second end, wherein said first end comprises two single stranded portions and said second end is double stranded, wherein one of said two single stranded portions is attached to a single binding partner, wherein said second end comprises a component-specific oligonucleotide barcode duplex sequence wherein said barcode sequence comprises a nucleic acid sequence unique to said component-specific binding partner, wherein said molecule does not have a fluorescent reporter.

2. The composition of claim 1, wherein said binding partner is selected from the group consisting of an antibody, a locked nucleic acid, a receptor, and a small organic molecule.

3. The composition of claim 1, wherein said first end further comprises a linker molecule.

4. The composition of claim 3, wherein said linker molecule attaches said first end to said binding partner.

5. A composition comprising a nucleic acid sequence, wherein said nucleic acid sequence comprises a 3'-5' first strand and a 5'-3' second strand, wherein said first strand and said second strand join a first intracellular component-specific oligonucleotide barcode and a second intracellular component-specific oligonucleotide barcode thereby forming an asymmetric barcode region wherein said first strand 3' end is attached to a single first binding partner having specific affinity for said first intracellular component and said second strand 3' end is attached to a single second binding partner having specific affinity for said second intracellular component, wherein said asymmetric barcode region comprises a nucleic acid sequence unique to said first and second intracellular components.

6. The composition of claim 5, wherein said first strand 3' end further comprises a first sequence complementary to a first primer.

7. The composition of claim 5, wherein said first strand 5' end further comprises a second sequence complementary to a second primer.

8. The composition of claim 5, wherein said first binding partner is selected from the group consisting of an antibody, a locked nucleic acid, a receptor, and a small organic molecule.

9. The composition of claim 5, wherein said second binding partner is selected from the group consisting of an antibody, a locked nucleic acid, a receptor, and a small organic molecule.

10. A kit, comprising:
   a) a first container comprising a plurality of forked adapter molecules comprising a first end and a second end, wherein said first end comprises two single stranded portions and said second end is double stranded, wherein one of said two single stranded portions is attached to a single binding partner, wherein said second end comprises a component-specific oligonucleotide barcode duplex sequence wherein said barcode sequence comprises a nucleic acid sequence unique to said component-specific binding partner, wherein said molecule does not have a fluorescent reporter.
   b) a second container comprising a solution capable of fixing a biological cell sample;
   c) a third container comprising buffers and reagents capable of supporting binding of said binding partner to intracellular components of said fixed biological cell sample; and
   d) a set of instructions describing: i) how to identify said intracellular components bound to said binding partners; and ii) construction of an intracellular component contact map.

11. The kit of claim 10, wherein said binding partners are selected from the group consisting of antibodies, locked nucleic acids, intracellular receptors, and small organic molecules.

12. A composition consisting of a first nucleic acid sequence comprising a first duplex region encoding a first barcode sequence unique to an attached first intracellular component binding partner, and a second nucleic acid sequence comprising a second duplex region encoding a second barcode sequence unique to an attached second intracellular component binding partner, and wherein said first and second binding partners have specific affinity for different intracellular components.

13. The composition of claim 12, wherein said first nucleic acid sequence or said second nucleic acid sequence comprise a phosphorylated blunt end.

14. The composition of claim 12, wherein said first nucleic acid sequence and said second nucleic acid sequence comprise a self-complementary sequence.

15. The composition of claim 12, wherein said first nucleic acid sequence comprises a first primer.

16. The composition of claim 15, wherein said first primer is a first sequencing primer.

17. The composition of claim 12, wherein said first nucleic acid sequence comprises a nucleic acid sequence complementary to a second primer.

18. The composition of claim 17, wherein said second primer is a second sequencing primer.

19. The composition of claim 12, wherein said first binding partner is selected from the group consisting of an antibody, a locked nucleic acid, a receptor, and a small organic molecule.

20. The composition of claim 12, wherein said second binding partner is selected from the group consisting of an antibody, a locked nucleic acid, a receptor, and a small organic molecule.

21. The composition of claim 12, wherein said ligated first and second nucleic acids comprise an asymmetric barcode region.

22. The composition of claim 21, wherein said asymmetric barcode region unambiguously identifies said different intracellular components.

23. A forked adapter molecule consisting of a first end and a second end, wherein said first end has two single stranded portions and said second end is double stranded, wherein one of said two single stranded portions is attached to a single binding partner, said binding partner having a specific affinity for a single intracellular component, wherein said second end is attached to an intracellular component-specific oligonucleotide barcode duplex sequence wherein said barcode sequence is a nucleic acid sequence unique to said intracellular component.

24. A nucleic acid sequence consisting of a 3'-5' first strand and a 5'-3' second strand, wherein said first strand and said second strand join a first intracellular component-specific oligonucleotide barcode and a second intracellular component-specific oligonucleotide barcode thereby forming an asymmetric barcode duplex region wherein said first strand 3' end is attached to a single first binding partner having specific affinity for said first intracellular component and said second strand 3' end is attached to a single second binding partner having specific affinity for said second intracellular component, wherein said asymmetric barcode duplex region is a nucleic acid sequence unique to said first and second intracellular components.

\* \* \* \* \*